(12) United States Patent
Shavit

(10) Patent No.: US 10,576,190 B2
(45) Date of Patent: Mar. 3, 2020

(54) SMART BAG USED IN SENSING PHYSIOLOGICAL AND/OR PHYSICAL PARAMETERS OF BAGS CONTAINING BIOLOGICAL SUBSTANCE

(71) Applicant: FreMon Scientific, Inc.

(72) Inventor: Menachem Shavit, Forest Hills, NY (US)

(73) Assignee: FreMon Scientific, Inc., La Jolla, CA (US)

( * ) Notice: Subject to any disclaimer, the term of this patent is extended or adjusted under 35 U.S.C. 154(b) by 389 days.

(21) Appl. No.: 15/502,642

(22) PCT Filed: Aug. 10, 2015

(86) PCT No.: PCT/US2015/044513
§ 371 (c)(1),
(2) Date: Mar. 7, 2017

(87) PCT Pub. No.: WO2016/023034
PCT Pub. Date: Feb. 11, 2016

(65) Prior Publication Data
US 2017/0239404 A1 Aug. 24, 2017

Related U.S. Application Data

(60) Provisional application No. 62/035,128, filed on Aug. 8, 2014, provisional application No. 62/035,162, filed
(Continued)

(51) Int. Cl.
*A61M 1/02* (2006.01)
*B01F 11/02* (2006.01)
(Continued)

(52) U.S. Cl.
CPC ......... *A61M 1/0281* (2013.01); *A01N 1/0263* (2013.01); *A61J 1/10* (2013.01);
(Continued)

(58) Field of Classification Search
CPC ... A61M 1/0281; A61M 1/025; A01N 1/0263; A61J 1/10; A61J 1/18; B01F 11/0005;
(Continued)

(56) References Cited

U.S. PATENT DOCUMENTS 2,640,906 A 6/1953 Haynes
3,485,245 A 12/1969 Lahr et al.
(Continued)

FOREIGN PATENT DOCUMENTS

CN 102802693 A 11/2012
DE 3121280 A1 1/1983
(Continued)

OTHER PUBLICATIONS

International Search Report and Written Opinion for PCT/US2015/044513, dated Jan. 5, 2016.
(Continued)

*Primary Examiner* — Jill A Warden
*Assistant Examiner* — Jacqueline Brazin
(74) *Attorney, Agent, or Firm* — Cooley LLP

(57) ABSTRACT

The present technology discloses a cost-effective, single use bag or container for storing biological substances that incorporates on its inner wall an electronic device that is configured to measure physiological and/or physical parameters of the enclosed biological substances, such as source history, identification, demographics, time stamping, temperature, pH, conductivity, glucose, $O_2$, $CO_2$ levels etc. The electronic device of the disclosed bag comprises a sensor configured to measure physiological and/or physical parameters of the biological substances enclosed within the bag, and a radio-frequency (RF) device communicably coupled to the sensor and configured to: (a) acquire from the sensor data associated with the measured parameters, (b) store the acquired
(Continued)

sensor data in nonvolatile memory, and (c) communicate the stored data wirelessly to a RF reader.

23 Claims, 16 Drawing Sheets

Related U.S. Application Data on Aug. 8, 2014, provisional application No. 62/035,152, filed on Aug. 8, 2014.

(51) Int. Cl.

| | |
|---|---|
| *A61J 1/10* | (2006.01) |
| *A61J 1/16* | (2006.01) |
| *B01F 11/00* | (2006.01) |
| *H05B 3/34* | (2006.01) |
| *A01N 1/02* | (2006.01) |
| *A61J 1/18* | (2006.01) |
| *B01F 15/06* | (2006.01) |
| *G01N 33/49* | (2006.01) |
| *H05B 1/02* | (2006.01) |

(52) U.S. Cl.
CPC . *A61J 1/16* (2013.01); *A61J 1/18* (2013.01); *A61M 1/025* (2013.01); *B01F 11/0005* (2013.01); *B01F 11/0266* (2013.01); *B01F 15/065* (2013.01); *G01N 33/492* (2013.01); *H05B 1/025* (2013.01); *H05B 3/34* (2013.01); *A61J 2200/42* (2013.01); *A61J 2200/70* (2013.01); *A61J 2200/72* (2013.01); *A61J 2205/60* (2013.01); *A61M 2205/3303* (2013.01); *A61M 2205/3368* (2013.01); *A61M 2205/3592* (2013.01); *A61M 2205/3633* (2013.01); *A61M 2205/3693* (2013.01); *A61M 2205/52* (2013.01); *A61M 2230/201* (2013.01); *A61M 2230/208* (2013.01); *B01F 2015/062* (2013.01); *B01F 2215/0034* (2013.01)

(58) Field of Classification Search
CPC . B01F 11/0266; B01F 15/065; G01N 33/492; H05B 1/025; H05B 3/34
USPC .......................................................... 436/55
See application file for complete search history.

(56) References Cited

U.S. PATENT DOCUMENTS

| | | | |
|---|---|---|---|
| 3,518,393 A | 6/1970 | Besseling et al. | |
| 3,590,215 A | 6/1971 | Anderson et al. | |
| 3,798,418 A | 3/1974 | Reik et al. | |
| 4,680,445 A | 7/1987 | Ogawa | |
| 4,731,072 A | 3/1988 | Aid | |
| 5,245,693 A | 9/1993 | Ford et al. | |
| 5,297,234 A | 3/1994 | Harms et al. | |
| 5,364,385 A | 11/1994 | Harms et al. | |
| H1623 H | 1/1997 | Reed et al. | |
| 5,616,268 A | 4/1997 | Carr | |
| 5,691,452 A | 11/1997 | Gawryl et al. | |
| 5,779,974 A | 7/1998 | Kuzyk | |
| 6,007,773 A | 12/1999 | Kuzyk | |
| 6,142,974 A | 11/2000 | Kistner et al. | |
| 6,259,067 B1 | 7/2001 | Faries, Jr. et al. | |
| 6,381,981 B1 | 5/2002 | Yaddgo et al. | |
| 6,384,380 B1 | 5/2002 | Faries, Jr. et al. | |
| 6,452,138 B1 | 9/2002 | Kochman et al. | |
| 6,596,531 B2 | 7/2003 | Campbell et al. | |
| 6,684,646 B2 | 2/2004 | Voute et al. | |
| 6,698,213 B2 | 3/2004 | Voute et al. | |
| 6,727,480 B2 | 4/2004 | Fernando et al. | |
| 6,748,164 B1 | 6/2004 | Kuzyk | |
| 6,786,054 B2 | 9/2004 | Voute et al. | |
| 6,824,528 B1 | 11/2004 | Faries, Jr. et al. | |
| 6,861,624 B1 | 3/2005 | Pelster | |
| 6,931,864 B2 | 8/2005 | Fuhr et al. | |
| 6,945,056 B2 | 9/2005 | Brown et al. | |
| 6,996,995 B2 | 2/2006 | Voute et al. | |
| 7,011,797 B2 | 3/2006 | Bakke | |
| 7,041,941 B2 | 5/2006 | Faries, Jr. et al. | |
| 7,077,559 B2 | 7/2006 | Hlavinka et al. | |
| 7,104,074 B2 | 9/2006 | Voute et al. | |
| 7,137,261 B2 | 11/2006 | Brown et al. | |
| 7,228,688 B2 | 6/2007 | Voute et al. | |
| 7,276,675 B2 * | 10/2007 | Faries, Jr. ............. | A61M 5/445 |
| | | | 219/413 |
| 7,278,278 B2 | 10/2007 | Wowk et al. | |
| 7,353,658 B2 | 4/2008 | Voute et al. | |
| 7,603,921 B2 | 10/2009 | Baumfalk et al. | |
| 7,618,808 B1 | 11/2009 | Papp | |
| 7,638,100 B2 | 12/2009 | Dawes | |
| 7,711,251 B2 | 5/2010 | Barkey | |
| 7,722,839 B2 | 5/2010 | Kuzyk | |
| 7,920,802 B2 | 4/2011 | Minagawa | |
| 7,924,169 B2 | 4/2011 | Baumfalk et al. | |
| 7,955,840 B2 | 6/2011 | Belgrader | |
| 7,958,791 B2 | 6/2011 | Zimmermann et al. | |
| 8,012,416 B2 * | 9/2011 | Kuzyk ..................... | H05B 3/82 |
| | | | 422/38 |
| 8,028,532 B2 | 10/2011 | Voute et al. | |
| 8,037,696 B2 | 10/2011 | Shaham et al. | |
| 8,070,354 B2 | 12/2011 | Bungay, III et al. | |
| 8,371,132 B2 | 2/2013 | Cutting et al. | |
| 8,377,030 B2 | 2/2013 | Hyde et al. | |
| 8,448,457 B2 | 5/2013 | Cutting et al. | |
| 8,451,138 B2 | 5/2013 | Zimmermann et al. | |
| 8,539,790 B1 | 9/2013 | Budd | |
| 8,550,703 B2 | 10/2013 | Cutting | |
| 8,852,536 B2 * | 10/2014 | Davidowitz ...... | G01N 35/00722 |
| | | | 422/565 |
| 8,863,532 B2 | 10/2014 | Voute et al. | |
| 8,968,232 B2 | 3/2015 | Kamen et al. | |
| 9,034,635 B2 | 5/2015 | Termaat et al. | |
| 9,046,292 B2 | 6/2015 | Burke et al. | |
| 9,103,703 B2 | 8/2015 | Baumfalk et al. | |
| 9,121,403 B2 | 9/2015 | Lanigan et al. | |
| 9,140,487 B2 | 9/2015 | Chaffey et al. | |
| 9,173,248 B2 | 10/2015 | Baker | |
| RE45,789 E | 11/2015 | Shei et al. | |
| 9,357,763 B2 | 6/2016 | Cullis et al. | |
| 9,441,893 B2 | 9/2016 | Velayudhan et al. | |
| 9,764,075 B2 | 9/2017 | Blickhan et al. | |
| 9,833,580 B2 | 12/2017 | Cho | |
| 10,023,833 B2 | 7/2018 | Akerstrom et al. | |
| 10,057,699 B2 | 8/2018 | Maggiore et al. | |
| 10,196,598 B2 | 2/2019 | Baust et al. | |
| 10,202,572 B2 | 2/2019 | Tanaka et al. | |
| 10,208,280 B2 | 2/2019 | Joaquim Rodrigues et al. | |
| 10,221,384 B2 | 3/2019 | Akerstrom et al. | |
| 10,232,331 B2 | 3/2019 | Boettcher et al. | |
| 10,251,389 B2 | 4/2019 | Kamieli et al. | |
| 2005/0126929 A1 | 6/2005 | Mansouri et al. | |
| 2006/0153549 A1 | 7/2006 | Cazzini et al. | |
| 2007/0029311 A1 | 2/2007 | Akashi et al. | |
| 2007/0217810 A1 | 9/2007 | Minagawa | |
| 2008/0310768 A1 * | 12/2008 | Hobson ............... | B65D 88/20 |
| | | | 383/33 |
| 2009/0009290 A1 | 1/2009 | Kneip et al. | |
| 2009/0026907 A1 | 1/2009 | Davidowitz et al. | |
| 2010/0075405 A1 | 3/2010 | Broadley et al. | |
| 2010/0291536 A1 * | 11/2010 | Viljoen ............. | A61B 10/0051 |
| | | | 435/4 |
| 2011/0082437 A1 * | 4/2011 | Stacey ................... | F25D 15/00 |
| | | | 604/404 |
| 2011/0127273 A1 | 6/2011 | Deane et al. | |
| 2011/0186517 A1 | 8/2011 | Hedmann et al. | |
| 2011/0198255 A1 | 8/2011 | Baumfalk et al. | |
| 2012/0234817 A1 | 9/2012 | Baker | |
| 2012/0330234 A1 | 12/2012 | Balluff et al. | |
| 2013/0304006 A1 | 11/2013 | Toth | |
| 2014/0071216 A1 | 3/2014 | Hu et al. | |

(56) References Cited

U.S. PATENT DOCUMENTS

| | | |
|---|---|---|
| 2015/0334774 A1 | 11/2015 | Schryver et al. |
| 2016/0106624 A1 | 4/2016 | Camisani et al. |
| 2016/0220748 A1 | 8/2016 | Pouchotflin |
| 2016/0243000 A1 | 8/2016 | Gray |
| 2017/0036181 A1 | 2/2017 | Boettcher et al. |
| 2017/0135902 A1 | 5/2017 | Scully, Jr. |
| 2017/0239404 A1 | 8/2017 | Shavit |
| 2017/0257908 A1 | 9/2017 | Schryver et al. |
| 2017/0277829 A1 | 9/2017 | Weggler et al. |
| 2018/0050856 A1 | 2/2018 | Baud et al. |
| 2018/0125754 A1 | 5/2018 | Sanchez et al. |
| 2018/0126345 A1 | 5/2018 | Topp-Manske |
| 2018/0127703 A1 | 5/2018 | Jarvius et al. |
| 2018/0147306 A1 | 5/2018 | Crawley et al. |
| 2018/0163164 A1 | 6/2018 | Husemann et al. |
| 2018/0177180 A1 | 6/2018 | Chapman et al. |
| 2018/0245031 A1 | 8/2018 | Sato et al. |
| 2018/0250666 A1 | 9/2018 | Paul et al. |
| 2018/0251715 A1 | 9/2018 | Paul et al. |
| 2018/0255766 A1 | 9/2018 | Dick et al. |
| 2018/0320126 A1 | 11/2018 | Doody |
| 2018/0324900 A1 | 11/2018 | Shavit |
| 2018/0360023 A1 | 12/2018 | McPherson et al. |
| 2019/0003939 A1 | 1/2019 | Milne et al. |
| 2019/0041308 A1 | 2/2019 | Schryver et al. |
| 2019/0048303 A1 | 2/2019 | Maggiore |
| 2019/0075786 A1 | 3/2019 | Milne et al. |
| 2019/0144811 A1 | 5/2019 | Heese et al. |
| 2019/0151519 A1 | 5/2019 | Shavit |
| 2019/0152676 A1 | 5/2019 | Murphy |
| 2019/0194593 A1 | 6/2019 | Ozaki et al. |

FOREIGN PATENT DOCUMENTS

| | | |
|---|---|---|
| DE | 3225695 A1 | 1/1984 |
| DE | 3311591 A1 | 10/1984 |
| DE | 3321603 A1 | 12/1984 |
| DE | 3640114 A1 | 6/1986 |
| DE | 3500614 A1 | 7/1986 |
| DE | 3705596 A1 | 9/1988 |
| DE | 3723861 A1 | 1/1989 |
| DE | 3741051 C1 | 6/1989 |
| DE | 3800283 A1 | 7/1989 |
| DE | 3900101 A1 | 7/1990 |
| DE | 4316163 C2 | 4/1995 |
| DE | 4328321 C2 | 6/1995 |
| DE | 19503350 C1 | 7/1996 |
| DE | 4444180 C2 | 4/1997 |
| DE | 19841556 C1 | 3/2000 |
| DE | 19940715 C2 | 12/2001 |
| DE | 10035297 A1 | 2/2002 |
| DE | 10112465 C1 | 7/2002 |
| DE | 10238492 A1 | 4/2004 |
| DE | 20-2004-017612 U1 | 1/2005 |
| DE | 10324116 A1 | 1/2005 |
| DE | 10332781 A1 | 2/2005 |
| DE | 10-2005-036369 A1 | 2/2007 |
| DE | 20-2005-021496 U1 | 5/2008 |
| DE | 10-2007-056169 A1 | 5/2009 |
| DE | 10-2009-011707 A1 | 6/2010 |
| DE | 10-2010-002895 A1 | 9/2011 |
| DE | 20-2013-101214 U1 | 4/2013 |
| DE | 20-2013-102927 U1 | 8/2013 |
| DE | 11-2015-000765 A5 | 11/2016 |
| DE | 10-2015-113325 A1 | 2/2017 |
| EP | 0 318 924 B1 | 3/1992 |
| EP | 1 138 304 A2 | 10/2001 |
| EP | 1 174 703 A2 | 1/2002 |
| EP | 1 426 672 A1 | 6/2004 |
| EP | 1 299 138 B1 | 10/2005 |
| EP | 1 441 585 B1 | 5/2006 |
| EP | 1 441 586 B1 | 6/2006 |
| EP | 1 747 790 B1 | 9/2007 |
| EP | 1 476 013 B1 | 5/2011 |
| EP | 2 547 386 A2 | 1/2013 |
| EP | 2 839 822 A1 | 2/2015 |
| EP | 2 914 104 A2 | 9/2015 |
| EP | 2 976 637 A1 | 1/2016 |
| EP | 2 442 857 B1 | 8/2016 |
| EP | 3 104 917 A1 | 12/2016 |
| EP | 3 016 553 B1 | 10/2017 |
| GB | 952521 A | 3/1964 |
| RU | 2552822 C1 | 6/2015 |
| WO | WO-88/07384 A1 | 10/1988 |
| WO | 2010031237 A1 | 3/2010 |
| WO | WO-2010/132627 A2 | 11/2010 |
| WO | WO-2011/113421 A2 | 9/2011 |
| WO | WO-2011/113421 A3 | 9/2011 |
| WO | WO-2014/146641 A1 | 9/2014 |
| WO | WO-2015/000464 A1 | 1/2015 |
| WO | WO-2015/120843 A1 | 8/2015 |
| WO | WO-2017/025789 A4 | 2/2017 |
| WO | WO-2018/000051 A1 | 1/2018 |
| WO | WO-2018/010999 A1 | 1/2018 |
| WO | WO-2018/025053 A1 | 2/2018 |
| WO | WO-2018/195107 A1 | 10/2018 |
| WO | WO-2018/211437 A1 | 11/2018 |

OTHER PUBLICATIONS

International Search Report and Written Opinion issued in International Application No. PCT/US18/25650 dated Jul. 2, 2018 (9 pages).

Extended European Search Report issued in corresponding European Application No. 15829831.5, dated Aug. 13, 2018, 8 pages.

Non-Final Office Action dated May 31, 2019, for U.S. Appl. No. 16/260,100, filed Jan. 28, 2019, 24 pages.

Non-Final Office Action dated Jul. 19, 2019, for U.S. Appl. No. 16/405,974, filed May 7, 2019, 9 pages.

* cited by examiner

SMART BAG USED IN SENSING PHYSIOLOGICAL AND/OR PHYSICAL PARAMETERS OF BAGS CONTAINING BIOLOGICAL SUBSTANCE

RELATED APPLICATIONS

This application is a national stage application, filed under 35 U.S.C. § 371, of PCT International Patent Application No. PCT/US2015/044513, filed on Aug. 10, 2015, and claims benefit of priority to U.S. Provisional Patent Application No. 62/035,128, filed on Aug. 8, 2014, U.S. Provisional Patent Application No. 62/035,162, filed on Aug. 8, 2014, and U.S. Provisional Patent Application No. 62/035,152, filed on Aug. 8, 2014, all of which, including their contents, are incorporated herein by reference in their entireties.

TECHNICAL FIELD

The present technology relates generally to the field of devices and methods used in detecting or monitoring physiological and/or physical parameters of bags containing biological substances.

BACKGROUND

Plasma, blood, blood products and medication bags are supplied by the millions to many medical facilities for transfusion on a daily basis. These bags are frozen and stored into inventory upon arrival and need to be thawed to no more than 36.6 C (97.99 F) before transfusion. Currently, these bags are not individually monitored for quality control. At best, evaluation of their contents is done off-line on sampled quantities. Thus, there are no routine procedures in place that can provide real-time information on the physiological and/or physical parameters of these stored biological substances from freezing to vein transfusion including source history, identification, demographics, time stamping, temperature, pH, conductivity, glucose, $O_2$, $CO_2$ levels etc. This situation is problematic because it creates opportunities for errors that can be harmful to patients.

The quality of frozen transfused materials depends on maintaining control over the thawing process. Underheating the substance may cause patients to experience hypothermia whereas overheating may cause severe damage (denaturation) to proteins and other components, thereby reducing the quality of the transfused fluid and endangering patients. With respect to plasma and glycerolized blood, current thawing devices are based on heat transfer through water bath or water bladders and are not capable of accurately detecting or monitoring the true temperature of plasma and glycerolized blood. Instead, these thawing devices can only provide thawing ambient temperature (i.e. water bath or water bladder temperature) and rely on a time dimension to ensure that the contents of the thawed bag is within the desired temperature range. Thus reproducible and consistent thawing results cannot be achieved without accurate temperature sensing of plasma, whole blood, glycerolized blood and red blood corpuscles. Consequently, there is a need for procedures that monitor the quality of drugs and biological substances during the freezing to vein transfusion life cycle.

SUMMARY

In one aspect, the present technology provides an enclosure for storing biological substances comprising a bag including an inner and an outer wall, the inner wall being in contact with biological substances, and an electronic device attached to the inner wall of the bag, including a sensor configured to measure physiological and/or physical parameters of the biological substances enclosed within the bag, and a radio-frequency (RF) device communicably coupled to the sensor and configured to: (a) acquire from the sensor data associated with the measured parameters, (b) store the acquired sensor data in nonvolatile memory, and (c) communicate the stored data wirelessly to a RF reader.

In some embodiments, the biological substance is fresh, frozen, stored, or thawed and is selected from the group consisting of: medication, plasma, whole blood, glycerolized blood, and red blood corpuscles (RBCs).

In some embodiments, the physical parameters of the biological substances include identification, source history, demographic data and time stamping. In some embodiments, the physiological parameters of the biological substances include temperature, pH, conductivity, glucose, $O_2$, $CO_2$ levels etc.

In some embodiments, the RF device is a radio-frequency identification (RFID) tag. In some embodiments, the RF device includes a wireless antenna or coil configured to receive power from and communicate with a RF reader. In some embodiments, the RF device includes nonvolatile memory configured to store parameters associated with the enclosed bag containing biological substances. In some embodiments, the RF device includes acquisition circuitry configured to acquire from the sensor data associated with the measured parameters. In some embodiments, the RFID tag is passive.

In some embodiments, the sensor is a temperature sensor that measures the temperature of the biological substances enclosed within the bag. In some embodiments, the temperature sensor is a traditional resistance temperature detector (RTD). In some embodiments, the temperature sensor is a thermistor. In some embodiments, the thermistor is a negative temperature coefficient (NTC) thermistor. In some embodiments, the biological substance is fresh, frozen, stored, or thawed and is selected from the group consisting of: medication, plasma, whole blood, glycerolized blood, and RBCs.

In another aspect, the present technology discloses a method for detecting or monitoring physiological and/or physical parameters of biological substances enclosed within a bag during the thawing process, comprising: (a) acquiring data associated with physical and/or physiological parameters of biological substances enclosed within a bag using a sensor, (b) storing the acquired sensor data on a RFID tag, and (c) communicating the stored data wirelessly to a RF reader.

In some embodiments, the biological substance is fresh, frozen, stored, or thawed and is selected from the group consisting of: medication, plasma, whole blood, glycerolized blood, and RBCs.

In some embodiments, the physical parameters of the biological substances include identification, source history, demographic data and time stamping. In some embodiments, the physiological parameters of the biological substances include temperature, pH, conductivity, glucose, $O_2$, $CO_2$ levels etc.

In some embodiments, the sensor is a temperature sensor that measures the temperature of the biological substances enclosed within the bag. In some embodiments, the temperature sensor is a traditional resistance temperature detector (RTD). In some embodiments, the temperature sensor is a thermistor. In some embodiments, the thermistor is a negative temperature coefficient (NTC) thermistor. In some embodiments, the biological substance is fresh, frozen, stored, or thawed and is selected from the group consisting of: medication, plasma, whole blood, glycerolized blood, and RBCs.

In some embodiments, the RFID tag is composed of a printed circuit board, an integrated circuit (IC) chip, a wireless antenna or coil to receive power from and communicate with a RF reader, nonvolatile memory configured to store parameters associated with the biological substances enclosed within the bag, and acquisition circuitry. In some embodiments, the RFID tag is passive.

In another aspect, the present technology discloses a method for monitoring the quality of biological substances enclosed within a bag during the freezing to vein transfusion life cycle, comprising: (a) acquiring data associated with physical and/or physiological parameters of biological substances enclosed within a bag using a sensor, (b) storing the acquired sensor data on a RFID tag, and (c) communicating the stored data wirelessly to a RF reader.

In some embodiments, the sensor is a temperature sensor that measures the temperature of the biological substances enclosed within the bag. In some embodiments, the temperature sensor is a traditional resistance temperature detector (RTD). In some embodiments, the temperature sensor is a thermistor. In some embodiments, the thermistor is a negative temperature coefficient (NTC) thermistor. In some embodiments, the biological substance is fresh, frozen, stored, or thawed and is selected from the group consisting of: medication, plasma, whole blood, glycerolized blood, and RBCs.

In some embodiments, the RFID tag is composed of a printed circuit board, an IC chip, a wireless antenna or coil to receive power from and communicate with a RF reader, nonvolatile memory configured to store parameters associated with the biological substances enclosed within the bag, and acquisition circuitry. In some embodiments, the RFID tag is passive.

In one aspect, the present technology provides a device attached to an outer wall of a bag containing biological substances and is configured to measure physiological and/or physical parameters of the bag, comprising a sensor configured to measure physiological and/or physical parameters of bags containing biological substances and a radio-frequency (RF) device communicably coupled to the sensor and configured to: (a) acquire from the sensor data associated with the measured parameters, (b) store the acquired sensor data in nonvolatile memory, and (c) communicate the stored data wirelessly to a RF reader.

In some embodiments, the biological substance is fresh, frozen, stored, or thawed and is selected from the group consisting of: medication, plasma, whole blood, glycerolized blood, and red blood corpuscles (RBCs).

In some embodiments, the physical parameters of the bags containing biological substances include identification, source history, demographic data and time stamping. In some embodiments, the physiological parameter of the bags containing biological substances includes temperature.

In some embodiments, the RF device is a radio-frequency identification (RFID) tag. In some embodiments, the RF device includes a wireless antenna or coil configured to receive power from and communicate with a RF reader. In some embodiments, the RF device includes nonvolatile memory configured to store parameters associated with the enclosed bag containing biological substances. In some embodiments, the RF device includes acquisition circuitry configured to acquire from the sensor data associated with the measured parameters. In some embodiments, the RFID tag is passive.

In some embodiments, the sensor is a temperature sensor that measures the temperature of the bags containing biological substances. In some embodiments, the temperature sensor is a traditional resistance temperature detector (RTD). In some embodiments, the temperature sensor is a thermistor. In some embodiments, the thermistor is a negative temperature coefficient (NTC) thermistor. In some embodiments, the biological substance is fresh, frozen, stored, or thawed and is selected from the group consisting of: medication, plasma, whole blood, glycerolized blood, and RBCs.

In another aspect, the present technology discloses a method for detecting or monitoring physiological and/or physical parameters of bags containing biological substances during the thawing process, comprising: (a) acquiring data associated with physical and/or physiological parameters of bags containing biological substances using a sensor, (b) storing the acquired sensor data on a RFID tag, and (c) communicating the stored data wirelessly to a RF reader.

In some embodiments, the biological substance is fresh, frozen, stored, or thawed and is selected from the group consisting of: medication, plasma, whole blood, glycerolized blood, and RBCs.

In some embodiments, the physical parameters of the bags containing biological substances include identification, source history, demographic data and time stamping. In some embodiments, the physiological parameter of the bags containing biological substances includes temperature.

In some embodiments, the sensor is a temperature sensor that measures the temperature of the bags containing biological substances. In some embodiments, the temperature sensor is a traditional resistance temperature detector (RTD). In some embodiments, the temperature sensor is a thermistor. In some embodiments, the thermistor is a negative temperature coefficient (NTC) thermistor. In some embodiments, the biological substance is fresh, frozen, stored, or thawed and is selected from the group consisting of: medication, plasma, whole blood, glycerolized blood, and RBCs.

In some embodiments, the RFID tag is composed of a printed circuit board, an integrated circuit (IC) chip, a wireless antenna or coil to receive power from and communicate with a RF reader, nonvolatile memory configured to store parameters associated with the bags containing biological substances, and acquisition circuitry. In some embodiments, the RFID tag is passive.

In another aspect, the present technology discloses a method for monitoring the quality of biological substances during the freezing to vein transfusion life cycle, comprising: (a) acquiring data associated with physical and/or physiological parameters of bags containing biological substances using a sensor, (b) storing the acquired sensor data on a RFID tag, and (c) communicating the stored data wirelessly to a RF reader.

In some embodiments, the sensor is a temperature sensor that measures the temperature of the bags containing biological substances. In some embodiments, the temperature sensor is a traditional resistance temperature detector (RTD). In some embodiments, the temperature sensor is a thermistor. In some embodiments, the thermistor is a negative temperature coefficient (NTC) thermistor. In some embodiments, the biological substance is fresh, frozen, stored, or thawed and is selected from the group consisting of: medication, plasma, whole blood, glycerolized blood, and RBCs.

In some embodiments, the RFID tag is composed of a printed circuit board, an IC chip, a wireless antenna or coil to receive power from and communicate with a RF reader, nonvolatile memory configured to store parameters associated with the bags containing biological substances, and acquisition circuitry. In some embodiments, the RFID tag is passive.

In one aspect, the present technology provides an enclosure for thawing bags containing biological substances comprising an overwrap bag having high thermal conductivity including an inner and an outer wall, and an electronic device attached to the inner wall of the overwrap bag, the electronic device configured to come into contact with an enclosed bag containing biological substances, including a sensor configured to measure physiological and/or physical parameters of the enclosed bag containing biological substances, and a radio-frequency (RF) device communicably coupled to the sensor and configured to: (a) acquire from the sensor data associated with the measured parameters, (b) store the acquired sensor data in nonvolatile memory, and (c) communicate the stored data wirelessly to a RF reader.

In some embodiments, the biological substance is fresh, frozen, stored, or thawed and is selected from the group consisting of: medication, plasma, whole blood, glycerolized blood, and red blood corpuscles (RBCs).

In some embodiments, the physical parameters of the biological substances include identification, source history, demographic data and time stamping. In some embodiments, the physiological parameter of the biological substances includes temperature.

In some embodiments, the RF device is a radio-frequency identification (RFID) tag. In some embodiments, the RF device includes a wireless antenna or coil configured to receive power from and communicate with a RF reader. In some embodiments, the RF device includes nonvolatile memory configured to store parameters associated with the enclosed bag containing biological substances. In some embodiments, the RF device includes acquisition circuitry configured to acquire from the sensor data associated with the measured parameters. In some embodiments, the RFID tag is passive.

In some embodiments, the sensor is a temperature sensor that measures the temperature of the enclosed bag containing biological substances. In some embodiments, the temperature sensor is a traditional resistance temperature detector (RTD). In some embodiments, the temperature sensor is a thermistor. In some embodiments, the thermistor is a negative temperature coefficient (NTC) thermistor. In some embodiments, the biological substance is fresh, frozen, stored, or thawed and is selected from the group consisting of: medication, plasma, whole blood, glycerolized blood, and RBCs.

In another aspect, the present technology discloses a method for detecting or monitoring physiological and/or physical parameters of an enclosed bag containing biological substances during the thawing process, comprising (a) acquiring data associated with physical and/or physiological parameters of an enclosed bag containing biological substances using a sensor, (b) storing the acquired sensor data on a RFID tag, and (c) communicating the stored data wirelessly to a RF reader.

In some embodiments, the biological substance is fresh, frozen, stored, or thawed and is selected from the group consisting of: medication, plasma, whole blood, glycerolized blood, and RBCs.

In some embodiments, the physical parameters of the enclosed bag containing biological substances include identification, source history, demographic data and time stamping. In some embodiments, the physiological parameter of the enclosed bag containing biological substances includes temperature.

In some embodiments, the sensor is a temperature sensor that measures the temperature of the enclosed bag containing biological substances. In some embodiments, the temperature sensor is a traditional resistance temperature detector (RTD). In some embodiments, the temperature sensor is a thermistor. In some embodiments, the thermistor is a negative temperature coefficient (NTC) thermistor. In some embodiments, the biological substance is fresh, frozen, stored, or thawed and is selected from the group consisting of: medication, plasma, whole blood, glycerolized blood, and RBCs.

In some embodiments, the RFID tag is composed of a printed circuit board, an integrated circuit (IC) chip, a wireless antenna or coil to receive power from and communicate with a RF reader, nonvolatile memory configured to store parameters associated with the enclosed bag containing biological substances, and acquisition circuitry. In some embodiments, the RFID tag is passive.

In one aspect, the present technology provides an apparatus for dry thawing a bag containing biological substances comprising a first cushion device and a second cushion device each including: (a) a flexible heat conducting sheet configured to make contact with a bag containing biological substances, (b) a high density heating element configured to supply thermal energy to the flexible heat conducting sheet, (c) a temperature sensor configured to make contact with and measure temperature of the bag, (d) a sonic vibrator assembly configured to sonically agitate the bag; and (e) a flexible non-heat conducting layer configured to promote unidirectional heat transfer towards the bag containing biological substances, and insulate the sonic vibrator assembly and the temperature sensor from the high density heating element; and (f) a heat insulation barrier configured to thermally isolate the temperature sensor from the flexible heat conducting sheet and the high density heating element, wherein the flexible heat conducting sheet of the first cushion device faces the flexible heat conducting sheet of the second cushion device.

In some embodiments, the apparatus of the present technology further comprises an electronic connector configured to supply electrical current to the temperature sensor, and the high density heating element.

In some embodiments, the biological substance is selected from the group consisting of: medication, plasma, whole blood, glycerolized blood, and RBCs.

In some embodiments, the heat insulation barrier is composed of material selected from the group consisting of: polystyrene foam, starch-based foams, cellulose, paper, rubber, non-woven material, wood, plastic and tin foil.

In some embodiments, the flexible heat conducting sheet is composed of silicon. In some embodiments, the perimeter of the flexible heat conducting sheet is larger than the perimeter of the bag containing biological substances. In some embodiments, the perimeter of the flexible heat conducting sheet is the same as the perimeter of the bag containing biological substances.

In some embodiments, the flexible non-heat conducting layer is composed of material selected from the group consisting of: polystyrene foam, starch-based foams, cellulose, paper, rubber, non-woven material, and plastic.

In some embodiments, the temperature sensor is a traditional resistance temperature detector (RTD). In some embodiments, the temperature sensor is a thermistor. In other embodiments, the temperature sensor is a negative temperature coefficient (NTC) thermistor. In some embodiments, the temperature sensor communicates the measured temperatures of the bag via the electronic connector during the thawing process.

In some embodiments, the high density heating element is configured to supply thermal energy to the flexible heat conducting sheet when powered with electrical current. In some embodiments, the high density heating element is configured to supply thermal energy that is sufficient to heat a 250-500 ml bag of biological substances with a starting temperature of −40° C. to 36.6° C. within 10 minutes. In other embodiments, the high density heating element is configured to supply thermal energy that is sufficient to heat a 250-500 ml bag of biological substances with a starting temperature of −40° C. to 36.6° C. within 5 minutes.

In another aspect, the present technology provides a method for dry thawing a bag containing biological substances comprising (a) driving electrical current through a high density heating element via an electronic connector, (b) transferring thermal energy generated by the high density heating element to a flexible heat conducting sheet, wherein the flexible heat conducting sheet is configured to diffuse thermal energy to a bag containing biological substances, (c) agitating the bag to achieve homogenous thawing using low frequency sonic vibrations, (d) measuring temperature of the bag using a temperature sensor, and (e) communicating the measurements via the electronic connector.

In some embodiments, the biological substance is selected from the group consisting of: medication, plasma, whole blood, glycerolized blood, and RBCs.

In some embodiments, the flexible heat conducting sheet is composed of silicon.

In some embodiments, the temperature sensor is a traditional resistance temperature detector (RTD). In some embodiments, the temperature sensor is a thermistor. In other embodiments, the temperature sensor is a negative temperature coefficient (NTC) thermistor. In some embodiments, the temperature sensor communicates the measured temperatures of the bag via the electronic connector during the thawing process.

In some embodiments, the high density heating element is configured to supply thermal energy that is sufficient to heat a 250-500 ml bag of biological substances with a starting temperature of −40° C. to 36.6° C. within 10 minutes. In other embodiments, the high density heating element is configured to supply thermal energy that is sufficient to heat a 250-500 ml bag of biological substances with a starting temperature of −40° C. to 36.6° C. within 5 minutes.

In some embodiments, the low frequency sonic vibrations range between 10 Hz to 50 Hz.

In one aspect, the present technology provides a computer-controlled apparatus for dry thawing bags containing biological substances, comprising (a) a first thawing chamber including: (i) a first cushion device and a second cushion device each including: (A) a flexible heat conducting sheet configured to make contact with a bag containing biological substances; (B) a high density heating element configured to supply thermal energy to the flexible heat conducting sheet; (C) a temperature sensor configured to make contact with and measure temperature of the bag; (D) a sonic vibrator assembly configured to sonically agitate the bag; (E) a flexible non-heat conducting layer configured to promote unidirectional heat transfer towards the bag containing biological substances, and insulate the sonic vibrator assembly and the temperature sensor from the high density heating element; and (F) a heat insulation barrier configured to thermally isolate the temperature sensor from the flexible heat conducting sheet and the high density heating element, wherein the flexible heat conducting sheet of the first cushion device faces the flexible heat conducting sheet of the second cushion device; and (ii) a radio frequency (RF) reader configured to wirelessly communicate with a radio-frequency identification device (RFID) tag on the bag; (b) a central controller configured to receive temperature data from the temperature sensor and the RF reader data, and control the high density heating element based on the received temperature data; and (c) a power supply configured to supply electrical current to the high density heating element based on control signals received from the central controller.

In some embodiments, the computer-controlled apparatus of the present technology further includes a plurality of thawing chambers identical to the first thawing chamber, wherein the plurality of thawing chambers are communicably coupled to the central controller. In some embodiments, the plurality of thawing chambers are part of the main module of the computerized closed-loop dry thawing system. In some embodiments, the main module of the computerized closed-loop dry thawing system has a two chamber configuration. In other embodiments, the main module of the computerized closed-loop dry thawing system has a four chamber configuration. In another embodiment, the main module of the computerized closed-loop dry thawing system has an eight chamber configuration.

In some embodiments, the central controller includes an expansion port configured to communicably couple with a plurality of auxiliary thawing chambers. In some embodiments, the number of auxiliary thawing chambers is two, four, six, eight, ten, or twelve.

In some embodiments, the bag is an overwrap bag including an inner and an outer wall; and an electronic device attached to the inner wall of the overwrap bag. In some embodiments, the electronic device is configured to come into contact with an enclosed bag containing biological substances and includes: (a) a sensor configured to measure physiological and/or physical parameters of the enclosed bag containing biological substances; and (b) a radio-frequency (RF) device communicably coupled to the sensor and configured to: (i) acquire from the sensor data associated with the measured parameters; (ii) store the acquired sensor data in nonvolatile memory; and (iii) communicate the stored data wirelessly to the RF reader.

In some embodiments, the bag is a container including an inner and an outer wall, the inner wall being in contact with biological substances; and an electronic device attached to the outer wall of the container, including: (a) a sensor configured to measure physiological and/or physical parameters of the container enclosing the biological substances; and (b) a radio-frequency (RF) device communicably coupled to the sensor and configured to: (i) acquire from the sensor data associated with the measured parameters; (ii) store the acquired sensor data in nonvolatile memory; and (iii) communicate the stored data wirelessly to the RF reader.

In some embodiments, the biological substance is selected from the group consisting of: medication, plasma, whole blood, glycerolized blood, and RBCs.

In some embodiments, the physical parameters include identification, source history, demographic data and time stamping. In some embodiments, the physiological parameter of the biological substances includes temperature.

In some embodiments, the RF device is a radio-frequency identification (RFID) tag. In some embodiments, the RF device includes a wireless antenna or coil configured to receive power from and communicate with a RF reader. In some embodiments, the RF device includes nonvolatile memory configured to store parameters associated with the bag. In some embodiments, the RF device includes acquisition circuitry configured to acquire from the sensor data associated with the measured parameters. In some embodiments, the RFID tag is passive.

In some embodiments, the flexible non-heat conducting layer is composed of material selected from the group consisting of: polystyrene foam, starch-based foams, cellulose, paper, rubber, non-woven material, and plastic.

In some embodiments, the heat insulation barrier is composed of material selected from the group consisting of: polystyrene foam, starch-based foams, cellulose, paper, rubber, non-woven material, wood, plastic and tin foil.

In some embodiments, the temperature sensor is a traditional resistance temperature detector (RTD). In some embodiments, the temperature sensor is a thermistor. In other embodiments, the temperature sensor is a negative temperature coefficient (NTC) thermistor.

In another aspect, the present technology discloses a computer controlled process for dry thawing biological substances comprising: (a) generating heat via a high density heating element, (b) diffusing heat generated by the high density heating element to a bag containing biological substances via a flexible heat conducting sheet, (c) agitating the bag to achieve homogenous thawing using low frequency sonic vibrations, (d) measuring temperature of the bag using a temperature sensor, (e) transmitting data associated with the measured temperatures to a central controller via an electrical connector, and (f) receiving, in response to (e), control signals for regulating the generation of heat by the high density heating element.

In some embodiments, the computer controlled process of the present technology further comprises (a) measuring temperature of the bag using a radio-frequency identification device (RFID) tag that is affixed to the bag, (b) receiving temperature data from a RF reader that is configured to wirelessly communicate with the RFID tag, and (c) receiving control signals from the central controller for regulating the high density heating element in response to (b).

In some embodiments, the low frequency sonic vibrations range between 10 Hz to 50 Hz.

In some embodiments, the biological substance is selected from the group consisting of: medication, plasma, whole blood, glycerolized blood, and RBCs.

In some embodiments, the bag is an overwrap bag including an inner and an outer wall; and an electronic device attached to the inner wall of the overwrap bag. In some embodiments, the electronic device is configured to come into contact with an enclosed bag containing biological substances and includes: (a) a sensor configured to measure physiological and/or physical parameters of the enclosed bag containing biological substances; and (b) a radio-frequency (RF) device communicably coupled to the sensor and configured to: (i) acquire from the sensor data associated with the measured parameters; (ii) store the acquired sensor data in nonvolatile memory; and (iii) communicate the stored data wirelessly to the RF reader.

In some embodiments, the bag is a container including an inner and an outer wall, the inner wall being in contact with biological substances; and an electronic device attached to the outer wall of the container, including: (a) a sensor configured to measure physiological and/or physical parameters of the container enclosing the biological substances; and (b) a radio-frequency (RF) device communicably coupled to the sensor and configured to: (i) acquire from the sensor data associated with the measured parameters; (ii) store the acquired sensor data in nonvolatile memory; and (iii) communicate the stored data wirelessly to the RF reader.

In some embodiments, the physical parameters include identification, source history, demographic data and time stamping. In some embodiments, the physiological parameter of the biological substances includes temperature.

In some embodiments, the RF device is a radio-frequency identification (RFID) tag. In some embodiments, the RF device includes a wireless antenna or coil configured to receive power from and communicate with a RF reader. In some embodiments, the RF device includes nonvolatile memory configured to store parameters associated with the bag. In some embodiments, the RF device includes acquisition circuitry configured to acquire from the sensor data associated with the measured parameters. In some embodiments, the RFID tag is passive.

In some embodiments, the heat insulation barrier is composed of material selected from the group consisting of: polystyrene foam, starch-based foams, cellulose, paper, rubber, non-woven material, wood, plastic and tin foil.

In some embodiments, the flexible non-heat conducting layer is composed of material selected from the group consisting of: polystyrene foam, starch-based foams, cellulose, paper, rubber, non-woven material, and plastic.

In some embodiments, the temperature sensor is a traditional resistance temperature detector (RTD). In some embodiments, the temperature sensor is a thermistor. In other embodiments, the temperature sensor is a negative temperature coefficient (NTC) thermistor.

DETAILED DESCRIPTION

Figure 1:
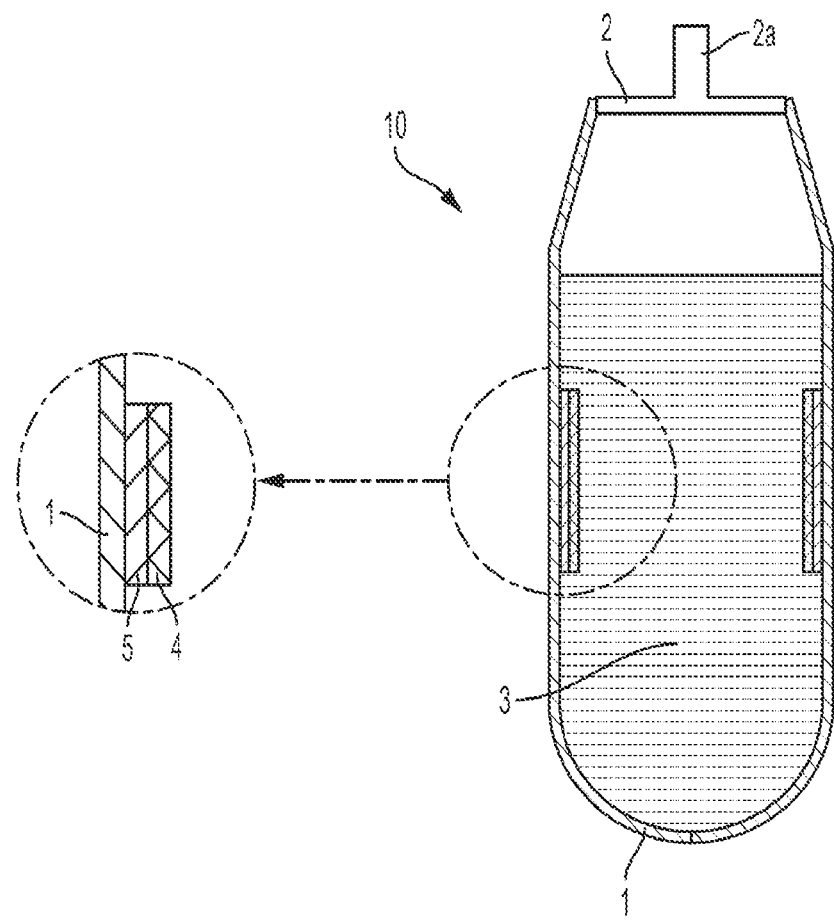
FIG. 1 shows a smart bag/container assembly.

The following description discusses apparatus and methods for dry thawing bags containing biological substances. Section A discusses a smart bag for containing the biological substances. Section B discusses a smart-label that can be affixed to a bag containing biological substances. Section C discusses overwrap bags that can be utilized to enclose other bags containing biological substances. Section C also discusses dry thawing chambers used for thawing bags, and modular dry thawing systems including multiple thawing chambers.

A. Smart Bag

Radio-frequency identification (RFID)

Radio-frequency identification (RFID) is the wireless non-contact use of radio-frequency electromagnetic fields to transfer data, for the purposes of automatically identifying and tracking tags attached to objects.

A RFID system uses tags, or labels attached to the objects to be identified. These tags contain information that is stored in memory. Two-way radio transmitter-receivers called interrogators or readers send a signal to the tag and read its response. RFID tags can be passive, active or battery-assisted passive. An active tag has an on-board battery and periodically transmits its ID signal. A battery-assisted passive (BAP) has a small battery on board and is activated when in the presence of a RF reader. A passive tag has no battery and must be powered by and read at short ranges via magnetic fields (electromagnetic induction) from an external source (i.e., a RF reader antenna). These tags then act as a passive transponder to emit microwaves or UHF radio waves (i.e., electromagnetic radiation at high frequencies), which the RF reader picks up and interprets as meaningful data. Passive tags must be illuminated with a power level roughly three magnitudes stronger than for signal transmission.

In some implementations, RFID tags can include an integrated circuit (IC) for storing and processing information, modulating and demodulating a radio-frequency (RF) signal, collecting DC power from the incident reader signal, and other specialized functions; and an antenna for receiving and transmitting the signal. The tag's components are enclosed within plastic, silicon or glass. The RFID tag includes either a chip-wired logic or a programmed or programmable data processor for processing the transmission and sensor data, respectively. Tags may either be read-only, having a factory-assigned serial number that is used as a key into a database, or may be read/write, where object-specific data can be written into the tag by the system user. Field programmable tags may be write-once, read-multiple. Data stored on RFID tags can be changed, updated and locked.

An RFID reader transmits an encoded radio signal to interrogate the tag. The RFID tag receives the message and then responds with its identification and other information. Signaling between the reader and the tag is done in several ways, depending on the frequency band used by the tag. Tags operating on LF and HF bands are, in terms of radio wavelength, very close to the reader antenna because they are only a small percentage of a wavelength away. In this near field region, the tag is closely coupled electrically with the transmitter in the reader. The tag can modulate the field produced by the reader by changing the electrical loading the tag represents. By switching between lower and higher relative loads, the tag produces a change that the reader can detect.

The RFID tag can be affixed to an object and can be read if passed near a reader, even if it is covered by the object or not visible. The tag can be read inside a case, carton, box or other container, and unlike barcodes, RFID tags can be read hundreds at a time. Furthermore, passive tags have low production costs and are manufactured to be disposable, along with the disposable consumer goods on which they are placed.

Temperature Sensors

Temperature sensors are devices used to measure the temperature of a medium by assessing some physical property which changes as a function of temperature (e.g., volume of a liquid, current through a wire). A commonly used temperature sensor is the resistance temperature detector (RTD). RTDs provide an electrical means of temperature measurement, and utilize the relationship between electrical resistance and temperature, which may be linear or nonlinear.

Figure 15:
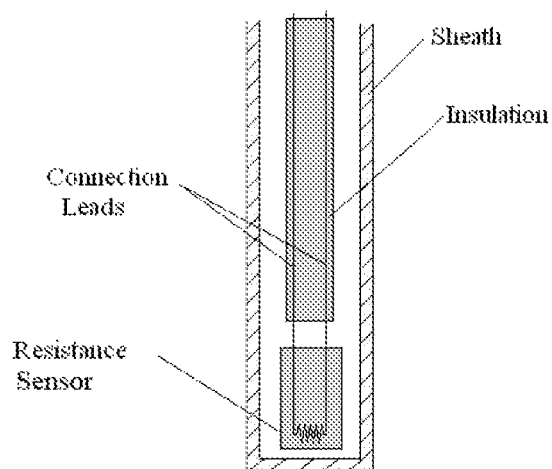
FIG. 15 shows a schematic of an example resistance temperature detector (RTD).

FIG. 15 shows a schematic of an example resistance temperature detector. As shown in FIG. 15, the RTD contains an outer sheath to prevent contamination from the surrounding medium. This sheath can be composed of material that efficiently conducts heat to the resistor, but resists degradation from heat or the surrounding medium. There are several categories of RTD sensors, such as, but not limited to: carbon resistors, film thermometers, wire-wound thermometers and coil elements. Sensors are most commonly composed of metals, such as platinum, nickel, or copper. The material chosen for the sensor determines the range of temperatures in which the RTD could be used. For example, platinum sensors, the most common type of resistor, have a range of approximately −200° C. to 800° C. Connected to the sensor are two insulated connection leads. These leads continue to complete the resistor circuit.

In some implementations, thermistors can be utilized as a temperature sensor. Thermistors can use a semiconductor, ceramic or polymer sensor, and can operate based upon the relationship between electrical resistance or these materials and the temperature. In some implementations, thermistors can exhibit high thermal sensitivity. Thermistors can be classified into two types: a positive temperature coefficient (PTC) thermistor, where the resistance increases with increasing temperature and a negative temperature coefficient (NTC) thermistor, where the resistance decreases with increasing temperature.

NTC thermistors are used mostly in temperature sensing and are made from a pressed disc, rod, plate, bead or cast chip of a semiconductor such as a sintered metal oxide. They work because raising the temperature of a semiconductor increases the number of active charge carriers in the conduction band. The more charge carriers that are available, the more current a material can conduct. The measurable electrical current can be sent to the microcontroller via a sensor interface circuitry. The microcontroller can process the received temperature readings into digital signals or values. The microcontroller may store and/or transmit these digital signals or values.

pH Sensors

A pH sensor is a device that measures the concentration of hydrogen ions in an aqueous solution. A liquid would be classified as acidic, alkaline or neutral according to its pH value. A pH measurement loop is made up of three components: the pH sensor; a preamplifier; and an analyzer or transmitter. A pH sensor is a potentiometric or electrochemical sensor that has a voltage output and consists of a measuring (glass) electrode, a reference electrode and a temperature sensor. The measuring electrode, which is sensitive to the presence of hydrogen ions, develops a potential (voltage) directly related to the hydrogen ion concentration of the solution. The reference electrode provides a stable potential against which the measuring electrode can be compared. When immersed in the solution, the reference electrode potential does not change with the changing hydrogen ion concentration. A solution in the reference electrode also makes contact with the sample solution and the measuring electrode through a junction, thereby completing the circuit. The electric potential created between the glass electrode, and the reference electrode is a function of the pH value of the measured solution. Thus a pH measurement loop is essentially a battery where the positive terminal is the measuring electrode and the negative terminal is the reference electrode.

The pH sensor components are usually combined into one device called a combination pH electrode. The measuring electrode is usually glass. Recent developments have replaced glass with more durable solid-state sensors. Additionally, the output of the measuring electrode changes with temperature even though the process remains at a constant pH. Thus a temperature sensor is necessary to correct for this change in output, and such calibration is accomplished via the analyzer or transmitter software. The preamplifier is a signal-conditioning device which takes the high-impedance pH electrode signal and changes it into a low impedance signal which the analyzer or transmitter can accept. The preamplifier also strengthens and stabilizes the signal, making it less susceptible to electrical noise. The sensor's electrical signal is then displayed via an analyzer or transmitter. The measurable electrical current can be sent to a microcontroller via a sensor interface circuitry. The microcontroller can process the received pH readings into digital signals or values. The microcontroller may store and/or transmit these digital signals or values. Additionally, the analyzer or transmitter can include a man-machine interface for calibrating the sensor and configuring outputs and alarms, if the pH is being regulated.

Glucose Sensors

A glucose sensor is a device that measures the approximate concentration of glucose in a blood sample. A consumable element containing chemicals that react with blood glucose is used for each measurement. In some implementations, this element is a plastic test strip with a small spot(s) impregnated with glucose oxidase, which catalyzes the oxidation of glucose to gluconolactone. In other implementations, the consumable element is a plastic test strip with a small spot(s) impregnated with glucose dehydrogenase (GDH), which oxidizes D-glucose to D-glucono-1,5-lactone.

In some implementations, the glucose sensors use an electrochemical method. Test strips contain a capillary that retrieves a reproducible amount of blood. The glucose in the blood reacts with an enzyme electrode containing glucose oxidase (or glucose dehydrogenase). The enzyme is reoxidized with an excess of a mediator reagent, such as a ferricyanide ion, a ferrocene derivative or osmium bipyridyl complex. The mediator in turn is reoxidized by reaction at the electrode, which generates an electrical current. The total charge passing through the electrode is proportional to the amount of glucose in the blood that has reacted with the enzyme. Some sensors employ the coulometric method which measures the total amount of charge generated by the glucose oxidation reaction over a period of time. Other glucose sensors use the amperometric method which measures the electrical current generated at a specific point in time by the glucose reaction. Both methods give an estimation of the concentration of glucose in the initial blood sample. The measurable electrical current can be sent to the microcontroller via a sensor interface circuitry. The microcontroller can process the received glucose levels into digital signals or values. The microcontroller may store and/or transmit these digital signals or values.

$CO_2$ Sensors

A $CO_2$ sensor is a device that measures the concentration of carbon dioxide gas. Most $CO_2$ sensors fall into one of two categories: nondispersive infrared gas sensors (NDIR) and chemical based gas sensors.

Figure 16:
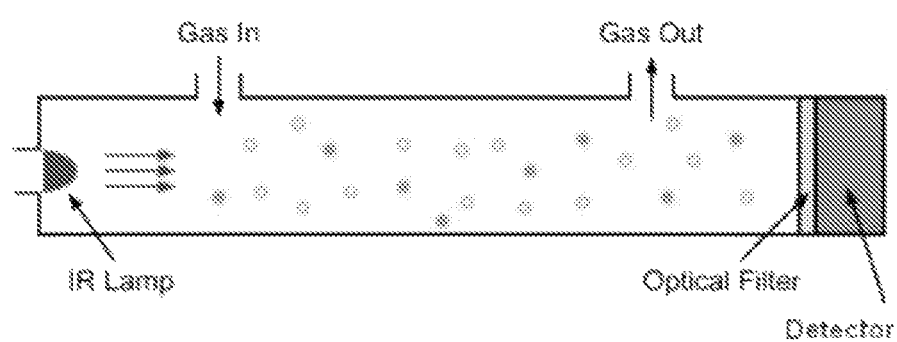
FIG. 16 shows a schematic of an example nondispersive infrared gas sensor.

FIG. 16 shows a schematic of an example nondispersive infrared gas sensor.

NDIR sensors are spectroscopic sensors used to detect $CO_2$ in a gaseous environment. These types of sensors consist of a tube or a chamber in which a source of infrared light is placed at one end and a detector at the other end. $CO_2$ gas is pumped or diffuses into the tube and the source directs the infrared waves of light in the tube filled with gas. The carbon dioxide molecules absorb light of a particular wavelength. An optical filter which is placed immediately in front of the detector absorbs the light except for the wavelength of light absorbed by carbon dioxide molecules. The difference between the amount of Infrared light at the source and the detector is measured by the electronics. This difference is directly proportional to the number of carbon dioxide molecules present in the gas. The microcontroller can process the received $CO_2$ levels into digital signals or values. The microcontroller may store and/or transmit these digital signals or values. NDIR $CO_2$ sensors can also be used for detecting dissolved $CO_2$ by coupling them to an ATR (attenuated total reflection) optic and measuring the gas in situ.

Figure 17:
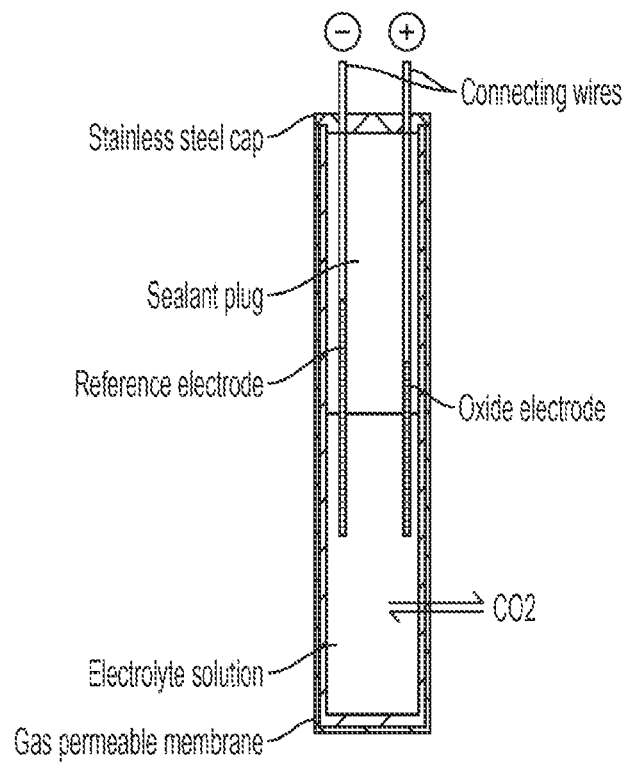
FIG. 17 shows a schematic of an example chemical based carbon dioxide sensor.

FIG. 17 shows a schematic of an example chemical based carbon dioxide sensor. The basic principle of chemical based carbon dioxide sensors is the measurement of the pH change of the electrolyte solution caused by the hydrolysis of the $CO_2$. The chemical based sensor consists of an oxide electrode, a reference electrode, a bicarbonate-based internal electrolyte solution, and a gas permeable membrane at the bottom of the sensor. The $CO_2$ molecules present in the solution diffuse through the gas permeable membrane and enter into the internal electrolyte solution. The carbon dioxide molecules react with the water to form carbonic acid, which again breaks into bicarbonate and proton ions.

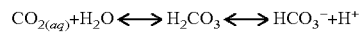
$$CO_{2(aq)} + H_2O \longleftrightarrow H_2CO_3 \longleftrightarrow HCO_3^- + H^+$$

These proton ions decrease the pH of the electrolyte solution, which is detected by the internal electrodes. The number of proton ions is directly proportional to the number of carbon dioxide molecules present. The measurable electrical current can be sent to the microcontroller via a sensor interface circuitry. The microcontroller can process the received $CO_2$ levels into digital signals or values. The microcontroller may store and/or transmit these digital signals or values.

$O_2$ Sensors

An $O_2$ sensor is a device that measures the concentration of oxygen in the gas or liquid being analyzed. The Clark-type electrode is the most used oxygen sensor for measuring oxygen dissolved in a liquid. The basic principle is that there is a cathode and an anode submersed in an electrolyte. Oxygen enters the sensor through a permeable membrane (e.g., Teflon) by diffusion, and is reduced at the cathode, creating a measurable electrical current. The relationship between the oxygen concentration and the electrical current is linear. The measurable electrical current can be sent to the microcontroller via a sensor interface circuitry. The microcontroller can process the received $O_2$ levels into digital signals or values. The microcontroller may store and/or transmit these digital signals or values.

Conductivity Sensors

An electrical conductivity sensor is a device that measures the ability of a solution to transfer (conduct) electric current. Conductivity is the reciprocal of electrical resistivity (ohms) and is therefore used to measure the concentration of dissolved solids which have been ionized in a polar solution.

In some implementations, conductivity sensors employ a potentiometric method which is based on induction. The potentiometric method employs four concentrically arranged electrodes: the outer two rings apply an alternating voltage and induce a current loop in the solution while the inner rings measure the voltage drop induced by the current loop. This measurement is directly dependent upon the conductivity of the solution. A shield around the rings maintains a constant field by fixing the volume of solution around the rings. In some embodiments, the electrodes are cylindrical and made of platinum metal. In other embodiments, the electrodes are made of stainless steel. While conductivity could theoretically be determined using the distance between the electrodes and their surface area using Ohm's law, a calibration using electrolytes of well-known conductivity is usually performed.

Another method of conductivity measurement uses an inductive method, sometimes referred to as a toroidal sensor. The sensor looks like a donut (toroid) on a stick and uses two toroidal transformers which are inductively coupled side by side and encased in a plastic sheath. A controller supplies a high frequency reference voltage to the first toroid or drive coil which generates a strong magnetic field. As the liquid containing conductive ions passes through the hole of the sensor, it acts as a one turn secondary winding. The passage of this fluid then induces a current proportional to the voltage induced by the magnetic field. The conductance of the one turn winding is measured according to Ohm's law. The conductance is proportional to the specific conductivity of the fluid and a constant factor determined by the geometry and installation of the sensor. The second toroid or receiving coil is also affected by the passage of the fluid in a similar fashion. The liquid passing through the second toroid also acts as a liquid turn or primary winding in the second toroidal transformer. The current generated by the fluid creates a magnetic field in the second toroid. The induced current from the receiving coil is measured as the output of the sensor. The controller converts the signal from the sensor to specific conductivity of the process liquid. The measurable electrical current can be sent to the microcontroller via a sensor interface circuitry. The microcontroller can process the received electrical conductivity into digital signals or values. The microcontroller may store and/or transmit these digital signals or values.

Hermetic Seals

Hermeticity is the process by which the internal environment of the critical components is made secure from invasion and contamination from the external environment, and is a function of both the bulk permeability of the chosen materials and the seal quality. The degree and measure of hermeticity is a function of materials choice, final seal design, fabrication processes and practices, and the use environment.

The choice of enclosures can span a large range of materials and involve numerous joining processes. Materials include metals such as nitinol, platinum, or MP35N or other stainless steels, and thin layers of metals such as nickel, gold, and aluminum. Other materials may include glass, ceramics ($Al_2O_3$), conductive epoxies, conformal coatings, silicones, Teflon and many plastics—for example, polyurethanes, silicones, and perfluorinated polymers. Similarly, joining processes vary from the use of adhesive sealants and encapsulants to fusion methods such as laser-beam welding or reflow soldering, or solid-state processes such as diffusion bonding. Plastics and laminates can be joined by a variety of methods including but not limited to impulse, heated-platen, radio-frequency (RF), dielectric, and ultrasonic sealing.

Smart Bag

FIG. 1 shows a smart bag/container assembly 10. The smart bag 1 includes a smart bag body 1, a smart bag cover 2, a smart bag inlet 2a, an electronic circuit layer 4 and a non-conductive heat-isolation layer 5. In some embodiments, the Smart bag or container 1 of the present technology can be soft, semi-rigid or rigid and can be made from materials such as plastic, metal thin sheet, or other materials and/or a combination thereof. In some embodiments, the cover 2 of the Smart bag or container is hermetically sealed to protect its contents 3. In some embodiments, the hermetic seal is composed of biologically inert material (e.g., epoxy). In some embodiments, the hermetically sealed cover 2 of the Smart bag or container contains an inlet 2a, wherein the inlet can be a valve, mechanical stopper, a spigot, or a plug. FIG. 1 shows an implementation where the cover 2 of the Smart bag 10 contains an inlet 2a. The inlet 2a ensures the sterile transfer of biological substances into and out of the Smart bag 10. In some embodiments, the Smart bag or container 10 is low-cost and disposable after a single use.

The Smart bag 10 can accommodate any volume of biological substances and can function in a wide ambient temperature range (−196° C. to +40° C.). In some embodiments, the biological substances are fresh, frozen, stored or thawed and are selected from the group consisting of medication, plasma, whole blood, glycerolized blood, and RBCs. FIG. 1 shows an implementation where a heat-isolation, nonconductive layer 5 can be printed on specific areas of the inner wall of the Smart bag 10. As shown in FIG. 1, an RFID tag containing an electronic circuit layer 4 (also known as a printed circuit board (PCB)) is printed or glued on the inner side of the heat-isolation, nonconductive layer 5 such that an attached sensor (e.g., temperature sensor, pH sensor, glucose sensor, oxygen sensor, carbon dioxide sensor, conductivity sensor) will be facing the opposite direction and is in direct contact with the fresh, frozen, stored or thawed biological substance 3 contained within the bag 10. Biological substances can be selected from the group consisting of medication, plasma, whole blood, glycerolized blood, and RBCs. Besides serving as an attachment site, the heat-isolation, nonconductive layer 5 helps reduce the impact of the ambient temperature on the readings of the RFID tag. The on-board electronics of the PCB are powered by electromagnetic induction from a RF reader antenna.

Figure 2:
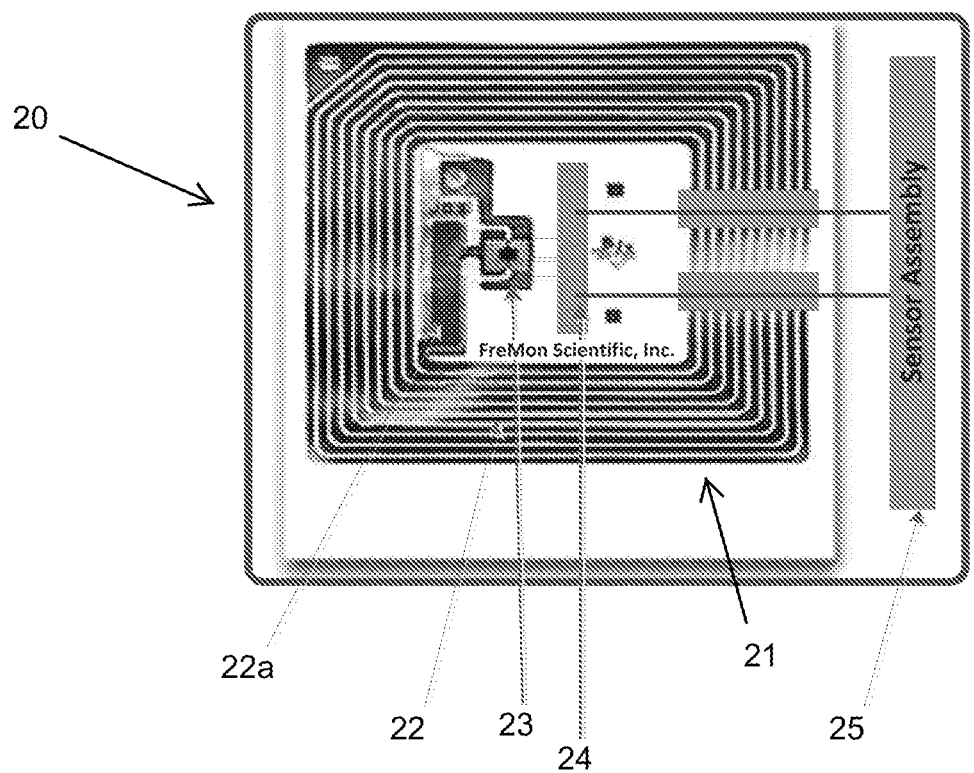
FIG. 2 shows an example smart bag electronic circuit layer (or PCB).

FIG. 2 shows an example smart bag electronic circuit layer (or PCB) 20. As shown in FIG. 2, the PCB layer 20 includes an RFID tag 21 communicably coupled to a sensor assembly 25 that can measure the physiological and/or physical parameters of biological substances contained within the Smart bag 10 shown in FIG. 1. The RFID tag-sensor coupling is achieved by integrating electronic components such as universal signal acquisition circuits (which read and acquire sensors data) on the PCB layer 20.

The PCB layer 20 can further include power interface circuitry 22a for receiving power from an RFID reader. In some implementations, the power interface circuitry can be coupled to an RF reader antenna 22 and harvest power from the voltage induced in the antenna 22 due to an RF signal received from the RF reader. In some implementations, the power interface circuitry 22a can include a rectifier for rectifying the A/C voltage appearing across the antenna into a D/C voltage. In some implementations, the power interface circuitry 22a may also include voltage step-up and voltage step-down circuitry for providing the desired voltages to various components on the PCB layer 20. The power interface circuitry 22a can be used to provide power to all the other circuitry included in the RFID tag 21, for example, the sensors, microcontrollers, memory, any interface circuitry, etc. In some implementations, the PCB 20 can be coupled to a battery to receive power in addition to or instead of receiving power as a result of an RF signal received from the RF reader.

The PCB 20 can also include a microcontroller or a microprocessor 23 for receiving and processing the sensor data received from the sensors 25 (e.g., temperature sensor, pH sensor, glucose sensor, oxygen sensor, carbon dioxide sensor, conductivity sensor etc., discussed above). In addition, the microcontroller 23 can also be utilized for carrying out communications with the external RFID reader. In some implementations, the microcontroller 23 can include a memory for storing executable instructions for processing and storing sensor data, for communicating with the external RF reader, etc. In some implementations, the memory can include nonvolatile memory configured to store sensed parameters associated with biological substances enclosed within Smart bags, and acquisition circuitry. For example the physiological parameters can include temperature, pH, conductivity, glucose, $O_2$, and $CO_2$ levels and the physical parameters can include identification, source history, demographic data and time stamping. In some implementations, the microcontroller or microprocessor 23 can be implemented using FPGAs (field-programmable gate arrays) or ASICs (application-specific integrated circuits).

A sensor interface circuitry 24 can be provided for the microcontroller 23 to interface with the sensor 25. In some implementations, the sensor interface circuitry 24 can include an analog-to-digital converter (ADC) for converting analog voltages/currents (representing the measured parameter) output by the sensor 25 into digital data. Such digital data can then be processed, stored, and/or transmitted by the microcontroller 23. In some implementations, the sensor interface circuitry 24 can be included within the microcontroller 23 itself.

During its operation, the RFID tag 21 stores the acquired sensor data in nonvolatile memory and communicates the stored data wirelessly to a RF reader. For instance, in one embodiment, the electronic device of the Smart bag can include thermistors and/or other temperature sensors (e.g., traditional RTDs) that contact and measure the temperature of the biological substances enclosed within the bag during the thawing process. The RFID tag 21 of the Smart bag will then store the temperature data associated with the enclosed biological substances in nonvolatile memory and will wirelessly communicate the stored data to a RF reader. Furthermore, because the RFID tag 21 facilitates accurate temperature sensing of the enclosed biological substances, the dangers of overheating and/or underheating during the thawing process are minimized. In some embodiments, the temperature sensor is a traditional resistance temperature detector (RTD). In some embodiments, the temperature sensor is a thermistor. In some embodiments, the thermistor is a negative temperature coefficient (NTC) thermistor.

In some embodiments, the sensor assembly 25 can include a pH sensor that measures the pH of the biological substances enclosed within the bag. In some embodiments, the sensor assembly 25 can include a glucose sensor that measures the glucose levels of the biological substances enclosed within the bag. In some embodiments, the glucose sensor uses glucose oxidase as the consumable element for each measurement. In some embodiments, the glucose sensor uses glucose dehydrogenase as the consumable element for each measurement. In some embodiments, the glucose sensor employs the coulometric method. In other embodiments, the glucose sensor employs the amperometric method.

In some embodiments, the sensor assembly 25 can include a $CO_2$ sensor that measures the $CO_2$ levels of the biological substances enclosed within the bag. In some embodiments, the $CO_2$ sensor assembly 25 can include a nondispersive infrared gas sensor (NDIR). In some embodiments, the $CO_2$ sensor is a chemical based gas sensor. In some embodiments, the sensor is an $O_2$ sensor that measures the $O_2$ levels of the biological substances enclosed within the bag. In some embodiments, the $O_2$ sensor is a Clark-type electrode.

In some embodiments, the sensor assembly 25 can include an electrical conductivity sensor that measures the ability of the biological substances enclosed within the bag to transfer (conduct) electric current. In some embodiments, the electrical conductivity sensor employs the potentiometric method. In other embodiments, the electrical conductivity sensor is a toroidal sensor.

B. Smart Label and Encapsulated Thin Container for Smart Bags

Smart Label

As used herein, the term Smart label refers to a device that includes one or more sensors configured to measure parameters of bags containing biological substances and a radiofrequency (RF) device (i.e., the RFID tag) communicably coupled to the sensor and configured to: (a) acquire from the sensor parameters associated with bags containing biological substances, (b) store the acquired sensor data in nonvolatile memory, and (c) communicate the stored data wirelessly to a RF reader.

In some embodiments, the label or encapsulated thin container of the present technology can be soft, semi-rigid or rigid and can be made from materials such as plastic, metal thin sheet, or other materials and/or a combination thereof. In some embodiments, the label is hermetically sealed. In some embodiments, the hermetic seal can be composed of biologically inert material (e.g., epoxy). In some embodiments, the label can be low-cost and disposable after a single use.

Hermeticity is the process by which the internal environment of the critical components is made secure from invasion and contamination from the external environment, and is a function of both the bulk permeability of the chosen materials and the seal quality. The degree and measure of hermeticity is a function of materials choice, final seal design, fabrication processes and practices, and the use environment.

The choice of enclosures can span a large range of materials and involve numerous joining processes. Materials include metals such as nitinol, platinum, or MP35N or other stainless steels, and thin layers of metals such as nickel, gold, and aluminum. Other materials may include glass, ceramics ($Al_2O_3$), conductive epoxies, conformal coatings, silicones, Teflon and many plastics—for example, polyurethanes, silicones, and perfluorinated polymers. Similarly, joining processes vary from the use of adhesive sealants and encapsulants to fusion methods such as laser-beam welding or reflow soldering, or solid-state processes such as diffusion bonding. Plastics and laminates can be joined by a variety of methods including but not limited to impulse, heated-platen, radio-frequency (RF), dielectric, and ultrasonic sealing.

Figure 3:
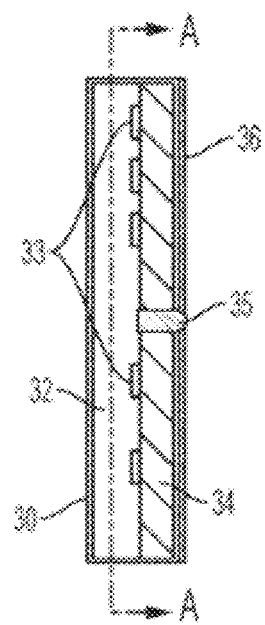
FIG. 3 shows a Smart label cross-section assembly.

The Smart label can function in a wide ambient temperature range (−196° C. to +40° C.). FIG. 3 shows a cross-sectional view of an implementation where a Smart label 30 can be affixed to an outer wall of a bag (not shown) containing biological substances. As shown in FIG. 3, an adhesive layer 36 is located on the same side as a temperature sensor 35. The adhesive layer 36 allows the smart label 30 to be affixed to the outer wall of the bag. In other implementations, the adhesive layer 36 and the temperature sensor 35 are located on opposite sides, thus allowing the Smart label 30 to be affixed to the inner wall of a bag containing biological substances. The bag containing the biological substances can be of any size. In some embodiments, the biological substances are fresh, frozen, stored or thawed and are selected from the group consisting of medication, plasma, whole blood, glycerolized blood, and RBCs.

FIG. 3 shows an implementation where the side of the Smart label 30, which interfaces with the ambient environment, is covered by a heat-isolation, nonconductive layer 32. The heat-isolation, nonconductive layer 32 helps reduce the impact of the ambient temperature on the readings of the Smart label 30. As shown in FIG. 3, the Smart Label 30 can include an RFID tag composed of a printed circuit board (PCB) 34 that is printed or glued on the inner side of the heat-isolation, nonconductive layer 32 such that an attached sensor (e.g., temperature sensor) 35 will be facing the opposite direction and is in contact with the bag or enclosure containing the fresh, frozen, stored or thawed biological substance. The biological substances may be selected from the group consisting of medication, plasma, whole blood, glycerolized blood, and RBCs. The on-board electronics 33 of the PCB 34 are powered by electromagnetic induction from a RF reader antenna.

Figure 4:
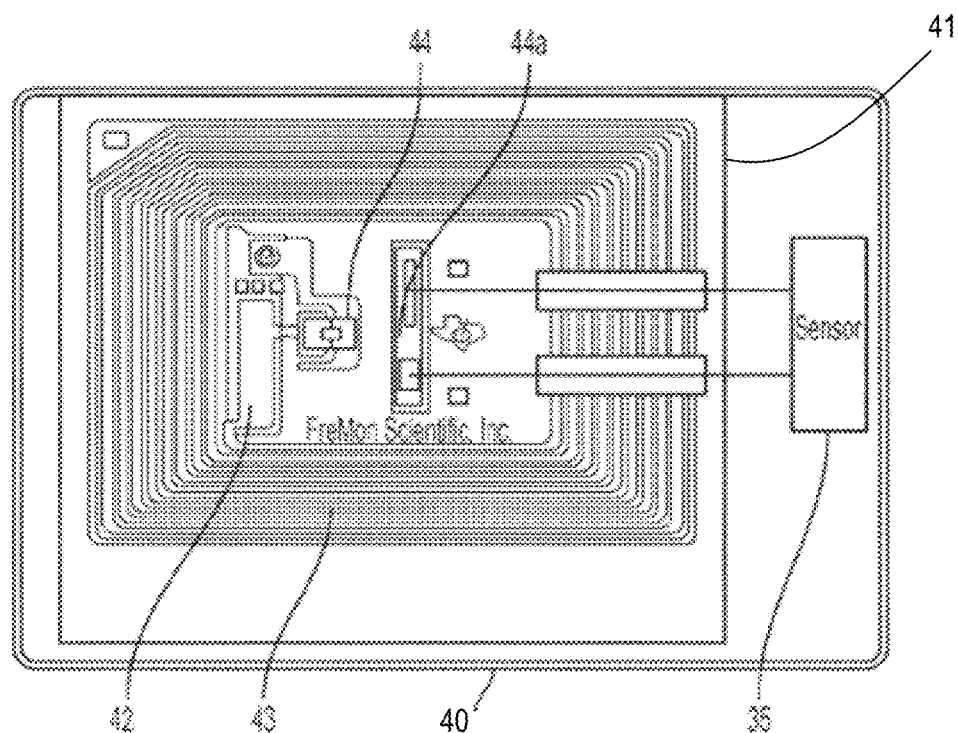
FIG. 4 shows a cross-sectional view of an example smart label printed circuit board (PCB) including an RFID tag.

FIG. 4 shows a cross-sectional view of an example smart label printed circuit board (PCB) 40 including an RFID tag 41. The PCB 40 can be used to implement the PCB 34 shown in FIG. 3. The PCB 40 can be affixed to an outer wall 46 of a bag containing biological substances. In some implementations, the PCB 40 can be instead affixed to an inner wall of the bag. As shown in FIG. 4, the RFID tag 41 is communicably coupled to a sensor 35 (also shown in FIG. 3) that can measure the physiological and/or physical parameters of bags containing biological substances. The RFID tag-sensor coupling is achieved by integrating electronic components such as universal signal acquisition circuits (which read and acquire sensors data) on the PCB layer 40.

The PCB 40 can further include power interface circuitry 42 for receiving power from an RFID reader. In some implementations, the power interface circuitry 42 can be coupled to an RF reader antenna 43 and harvest power from the voltage induced in the antenna due to an RF signal received from the RF reader. In some implementations, the power interface circuitry 42 can include a rectifier for rectifying the A/C voltage appearing across the antenna into a D/C voltage. In some implementations, the power interface circuitry 42 may also include voltage step-up and voltage step-down circuitry for providing the desired voltages to various components on the PCB 40. The power interface circuitry can be used to provide power to all the other circuitry included in the RFID tag 41, for example, the sensors, microcontrollers, memory, any interface circuitry, etc. In some implementations, the PCB 40 can be coupled to a battery to receive power in addition to or instead of receiving power as a result of an RF signal received from the RF reader.

The PCB 40 can also include a microcontroller or a microprocessor 44 for receiving and processing the sensor data received from the sensors 35 (e.g., temperature sensor). In addition, the microcontroller 44 can also be utilized for carrying out communications with the external RFID reader. In some implementations, the microcontroller 44 can include a memory for storing executable instructions for processing and storing sensor data, for communicating with the external RF reader, etc. In some implementations, the memory can include nonvolatile memory configured to store sensed parameters associated with bags containing biological substances, and acquisition circuitry. For example the physiological parameters can include temperature and the physical parameters can include identification, source history, demographic data and time stamping. In some implementations, the microcontroller or microprocessor 44 can be implemented using FPGAs (field-programmable gate arrays) or ASICs (application-specific integrated circuit).

A sensor interface circuitry 44a can be provided for the microcontroller 44 to interface with the sensor 35. In some implementations, the sensor interface circuitry 44a can include an analog-to-digital converter (ADC) for converting analog voltages/currents (representing the measured parameter) output by the sensor into digital data. Such digital data can then be processed, stored, and/or transmitted by the microcontroller 44. In some implementations, the sensor interface circuitry 44a can be included within the microcontroller 44 itself.

During its operation, the RFID tag 41 stores the acquired sensor data in nonvolatile memory and communicates the stored data wirelessly to a RF reader. For instance, in one embodiment, the Smart label comprises of thermistors and/or other temperature sensors (e.g., traditional RTDs) that contact and measure the temperature of bags containing biological substances during the thawing process. The RFID tag 41 of the Smart label will then store the temperature data associated with the bags containing biological substances in nonvolatile memory and will wirelessly communicate the stored data to a RF reader. Because the RFID tag of the Smart label facilitates accurate temperature sensing of bags containing biological substances, the dangers of overheating and/or underheating during the thawing process are minimized. In some embodiments, the temperature sensor is a traditional resistance temperature detector (RTD). In some embodiments, the temperature sensor is a thermistor. In some embodiments, the thermistor is a negative temperature coefficient (NTC) thermistor.

Figure 5:
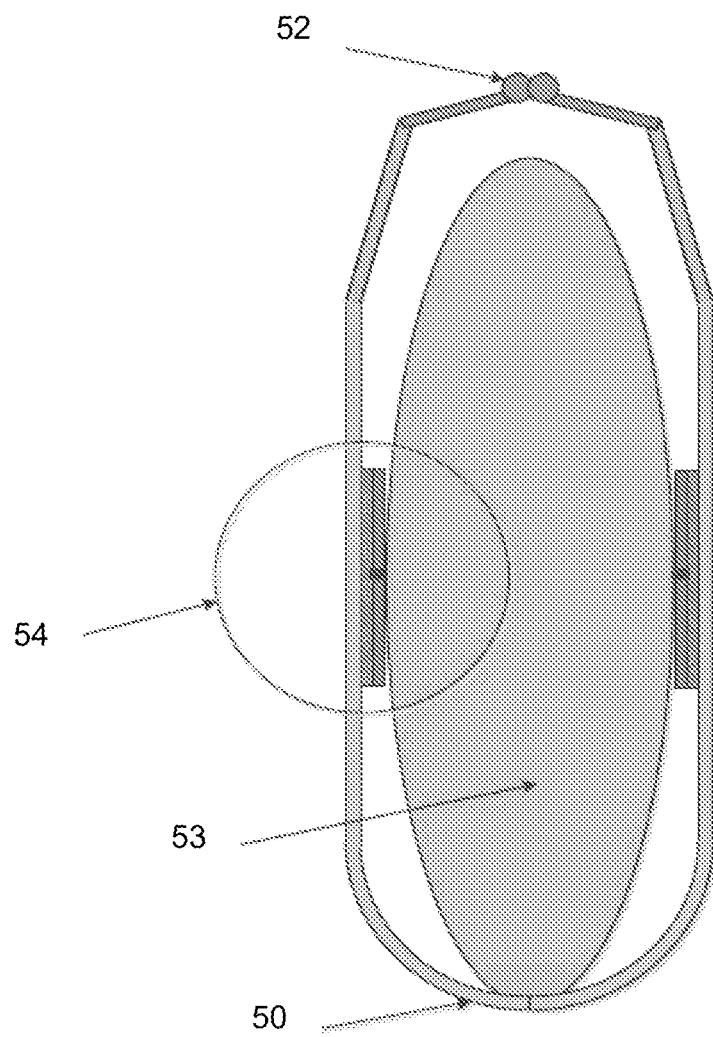
FIG. 5 shows an example Smart Overwrap Bag.

C. Devices and Methods for Thawing Frozen Bags Containing Biological Substances Using Dry Heating Smart Overwrap Bag FIG. 5 shows and example Smart overwrap bag 50. The Smart overwrap bag 50 can be composed of materials having high thermal conductivity such as plastic, metal thin sheet, other known thermal conductors, and/or a combination thereof, and can function in a wide ambient temperature range (−196° C. to +40° C.). The Smart overwrap bag 50 can be routinely used to enclose and protect bags 53 containing biological substances from microbial contamination during the thawing process. In the event that the bag 53 containing biological substances leaks or breaks during the thawing process, the overwrap bag 50 isolates the biological contents, thereby preventing them from contaminating the thawing device or system.

The overwrap bag 50 can enclose a bag containing biological substances of any size (e.g., 250-500 ml). In some embodiments, the overwrap bag 50 can be soft, semi-rigid or rigid and its cover can hermetically sealed to protect its contents. In some embodiments, the hermetic seal is composed of biologically inert material (e.g., epoxy). In some embodiments, an engaging mechanism at the opening of the overwrap bag 50 may be used to remove the bag containing biological substances after the thawing process is complete. FIG. 5 shows an implementation where the engaging mechanism at the opening of the overwrap bag is a ziplock 52. In some embodiments, the overwrap bag 50 can be low-cost and can be disposable after a single use.

In some embodiments, the overlap bag 50 can have high thermal conductivity. The high thermal conductivity of the overwrap bag 50 can facilitate rapid thawing of the enclosed bags 53 containing biological substances. In some embodiments, a dry thawing method can be used for thawing the enclosed bag 53. In other embodiments, conventional water-bath or water bladder methods can also be used. In some embodiments, mechanical agitation can be used during the thawing method to achieve a homogenous temperature profile within the enclosed bag 53 containing biological substances and to prevent damage to the biological substances. In some embodiments, the biological substances can be fresh, frozen, stored or thawed and can include medication, plasma, whole blood, glycerolized blood, and RBCs. In some embodiments, the overlap bag 50 can include one or more temperature sensing modules 54 for sensing the temperature of the enclosed bag 53.

Figure 6:
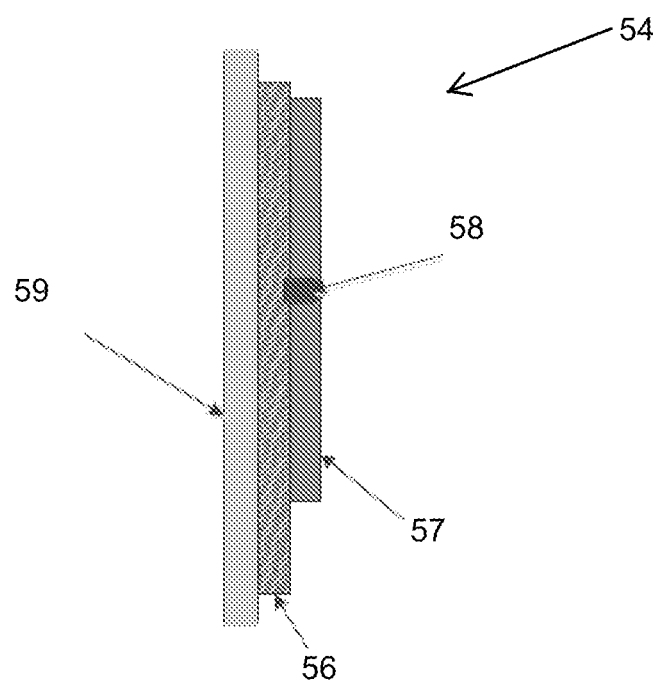
FIG. 6 shows an example temperature sensing module that can be included in an overlap bag, such as the one shown in FIG. 5.
Figure 7:
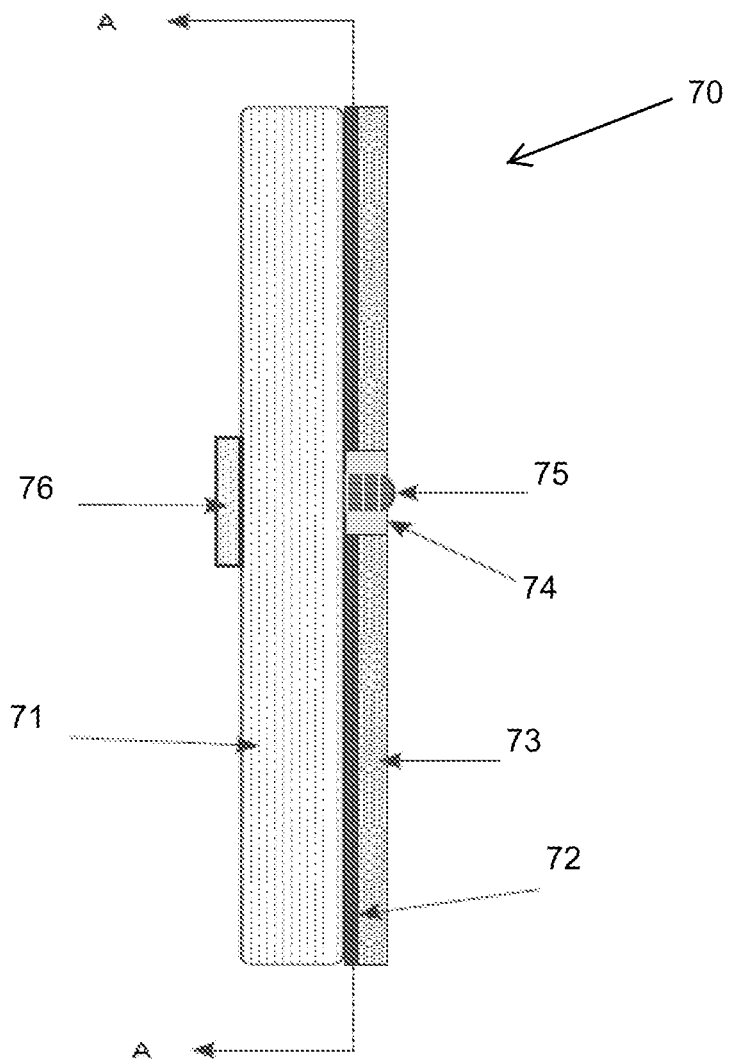
FIG. 7 shows the side view of an example thawing cushion device.

FIG. 6 shows an example temperature sensing module 54 that can be included in an overlap bag, such as the one shown in FIG. 5. In some implementations, the temperature sensing module 54 can be similar to the Smart label 30 discussed above in relation to FIG. 3. The temperature sensing module 54 can include a heat-conductive layer 56, an electronic circuit 57, and a temperature sensor 58. As shown in FIG. 6, the heat-nonconductive layer 56 can be printed or disposed on specific areas of an inner wall 59 of the overwrap bag. The inner wall 59 of the overlap bag can also be in contact with the outer wall of the enclosed bag containing biological substances (such as the enclosed bag 53 shown in FIG. 5). According to FIGS. 6 and 7, an RFID tag containing an electronic circuit layer (or a printed circuit board (PCB)) is printed or glued on the inner side of the heat-nonconductive layer such that an attached sensor (e.g., temperature sensor) will be facing the opposite direction and is in contact with the bag containing the fresh, frozen, stored or thawed biological substance. Biological substances can be selected from the group consisting of medication, plasma, whole blood, glycerolized blood, and RBCs. Besides serving as an attachment site, the heat-nonconductive layer helps reduce the impact of the ambient temperature on the readings of the RFID tag. The on-board electronics of the PCB are powered by electromagnetic induction from a RF reader antenna. As shown in FIG. 7, the RFID tag is communicably coupled to a sensor that will measure the physiological and/or physical parameters of the enclosed bags containing biological substances. The RFID tag-sensor coupling is achieved by integrating electronic components such as universal signal acquisitions (which read and acquire sensor data) on the PCB layer.

The PCB can further include power interface circuitry for receiving power from the RFID reader. In some implementations, the power interface circuitry can be coupled to the RF reader antenna and harvest power from the voltage induced in the antenna due to an RF signal received from the RF reader. In some implementations, the power circuitry can include a rectifier for rectifying the A/C voltage appearing across the antenna into a D/C voltage. In some implementations, the power circuitry may also include voltage step-up and voltage step-down circuitry for providing the desired voltages to various components on the PCB. The power circuitry can be used to provide power to all the other circuitry included in the RFID tag, for example, the sensors, microcontrollers, memory, any interface circuitry, etc. In some implementations, the PCB can be coupled to a battery to receive power in addition to or instead of receiving power as a result of an RF signal received from the RF reader.

The PCB can also include a microcontroller or a microprocessor for receiving and processing the sensor data received from the sensors (e.g., temperature sensor). In addition, the microcontroller can also be utilized for carrying out communications with the external RFID reader. In some implementations, the microcontroller can include a memory for storing executable instructions for processing and storing sensor data, for communicating with the external RF reader, etc. In some implementations, the memory can include nonvolatile memory configured to store sensed parameters associated with enclosed bags containing biological substances during the thawing process, and acquisition circuitry. For example the physiological parameters can include temperature and the physical parameters can include identification, source history, demographic data and time stamping. In some implementations, the microcontroller or microprocessor can be implemented using FPGAs (field-programmable gate arrays) or ASICs (application-specific integrated circuits).

A sensor interface circuitry can be provided for the microcontroller to interface with the sensor. In some implementations, the sensor interface circuitry can include an analog-to-digital converter (ADC) for converting analog voltages/currents (representing the measured parameter) output by the sensor into digital data. Such digital data can then be processed, stored, and/or transmitted by the microcontroller. In some implementations, the sensor interface circuitry can be included within the microcontroller itself.

During its operation, the RFID tag stores the acquired sensor data in nonvolatile memory and communicates the stored data wirelessly to a RF reader. For instance, in one embodiment, the electronic device of the overwrap bag comprises of thermistors and/or other temperature sensors (e.g., traditional RTDs) that contact and measure the temperature of enclosed bags containing biological substances during the thawing process. The RFID tag of the overwrap bag will then store the temperature data associated with the enclosed bags containing biological substances in nonvolatile memory and will wirelessly communicate the stored data to a RF reader. Because the RFID tag facilitates accurate temperature sensing of the enclosed bags containing biological substances, the dangers of overheating and/or underheating during the thawing process are minimized. In some embodiments, the temperature sensor is a traditional resistance temperature detector (RTD). In some embodiments, the temperature sensor is a thermistor. In some embodiments, the thermistor is a negative temperature coefficient (NTC) thermistor.

In some implementations, the RFID tag may be implemented on a system-on-chip (SOC). In some other implementations, the RFID tag may be implemented using discrete components.

In some embodiments, a Smart label, similar to the Smart label 30 discussed above in relation to FIG. 3 can be utilized as a sensing module within the overlap bag 50 shown in FIG. 5.

Cushion Device

Figure 10:
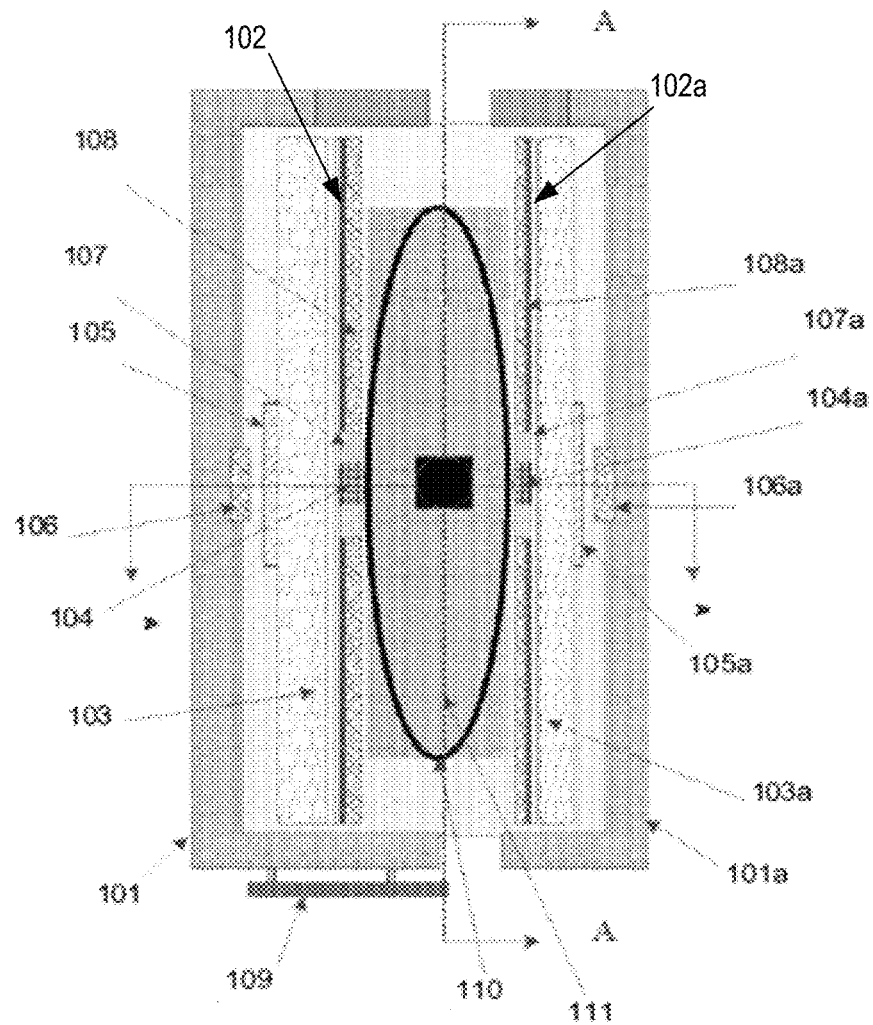
FIG. 10 shows the top view of the dry heat thawing chamber.

The present technology provides a device and method for thawing bags of biological substances without the use of water baths or water bladders. FIG. 7 shows a side view of an example dry thawing cushion device 70. In particular, the cushion device includes a flexible non-heat conducting layer, i.e., the cushion 71 that is affixed to a sonic vibrator assembly 76 on its outer side, and a printed circuit board (not shown) on its inner side. The printed circuit board on the inner side of the cushion interfaces with a heating element 72 and one or more temperature sensors 75. As shown in FIG. 10, the heating element 72 is attached to a flexible heat conducting sheet 73, the flexible heat conducting sheet 73 being configured to come into contact with a bag containing biological substances. Additionally FIG. 10 shows one or more temperature sensors 75 placed in or around the center on the inner side of the cushion, which are configured to (a) make contact with the bag in need of thawing and (b) periodically measure the temperature of the bag during the thawing process. In some embodiments, the temperature sensor 75 can be a traditional resistance temperature detector (RTD). In some embodiments, the temperature sensor can be a thermistor. In some embodiments, the thermistor can be a negative temperature coefficient (NTC) thermistor.

In some embodiments, the cushion device 70 can include two cushion devices facing each other, such that the two cushion devices can thaw a bag containing biological substances. The two cushion devices can have dimensions that are configured to contact a standard 250 ml-500 ml bag containing medication, plasma, whole blood, glycerolized blood bag, RBCs and/or other biological substances. Additionally, the flexible nature of the cushion materials ensure that bags or containers for biological substances of larger sizes can be accommodated within the space between the two flexible heat conducting sheets of the first and second cushion devices.

Figure 14:
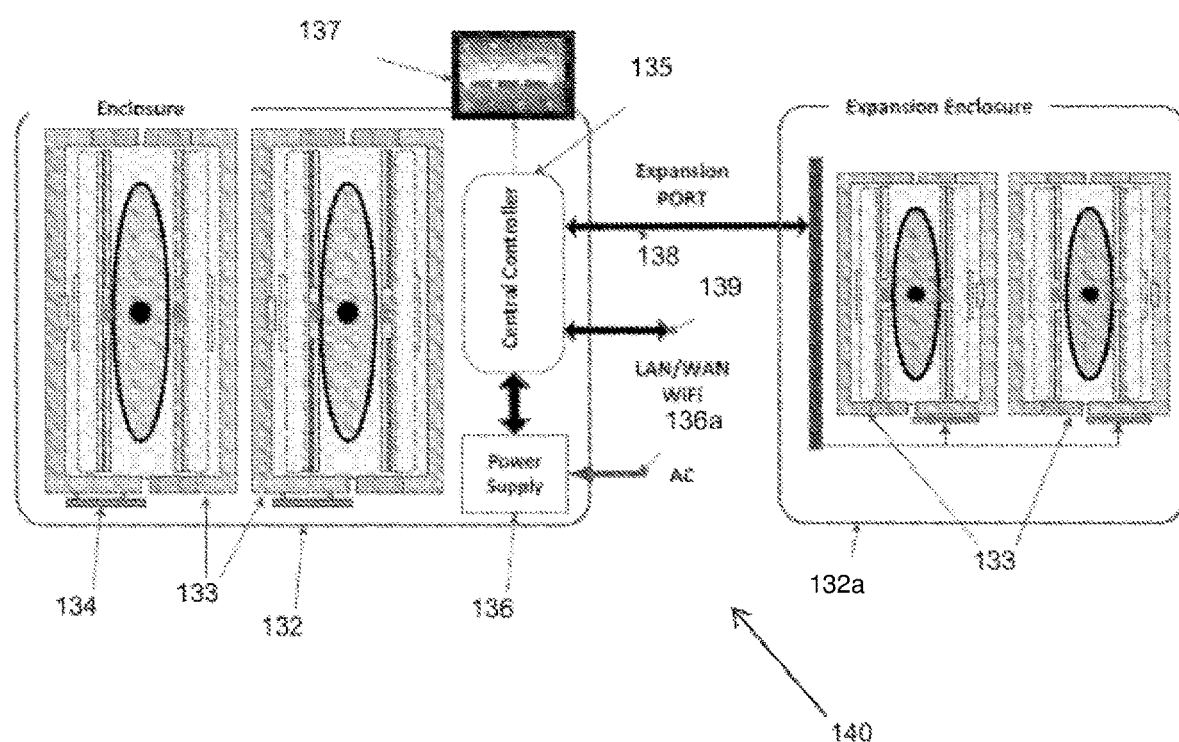
FIG. 14 is a block diagram of an expanded device from two to four thawing chambers (top view).

In some embodiments, the cushion 71 can be composed of materials that have low thermal conductivity, and can include, without limitation, materials such as polystyrene foam, starch-based foams, cellulose, paper, rubber, non-woven material, and plastic. As seen in FIGS. 7 and 14, the cushion 71 insulates the sonic vibrator 76 assembly and temperature sensor 75 from the thermal energy generated by the heating element 72. The cushion 71 thus serves a dual purpose: protecting the sonic vibrator assembly 76 and temperature sensor 75 from thermal damage and facilitating efficient unidirectional heat transfer from the heating element 72 to the flexible heat conducting sheet 73 to the bag of biological substances that requires thawing.

In some embodiments, the heating element 72 located between the cushion 71 and the flexible heat conducting sheet 73 is a high density, low-power heating element.

In some embodiments, the flexible heat conducting sheet 73 is thin and composed of silicon or other materials with similar thermal conductivity properties. FIG. 16 shows an implementation where the flexible heat conducting sheet is transparent. In other implementations, the flexible heat conducting sheet is opaque or translucent.

As shown in FIGS. 7 and 14, the temperature sensor 75 is placed in clearance of the flanking heating element 72 and the flexible heat conducting sheet 73 in order to prevent thermal damage to the sensor 75. As shown in FIG. 7, the temperature sensor 75 can be also mounted on and surrounded by heat insulation barriers 74 with the above clearance dimensions. The presence of the heat insulation barriers 74 can minimize the impact of the heating element 72 and flexible heat conducting sheet 73 on the temperature sensor 75 readings. In some embodiments, the heat insulation barriers 74 are composed of materials including, but not limited to polystyrene foam, starch-based foams, cellulose, paper, rubber, non-woven material, wood, plastic and tin foil.

While mechanical agitation is routinely used to expedite thawing, conventional thawing devices that employ this technique often consist of moving components that generate unwanted noise. The sonic vibrator assembly 76 discussed below generates low frequency (10 Hz-50 Hz) vibrations to achieve homogenous thawing within the bag containing biological substances. These low frequency vibrations are barely perceptible to the human ear, thereby circumventing the need to use audible mechanical moving mechanisms that cause noise. As shown in FIG. 7, the sonic vibrator assembly 76 is affixed to the outer side of the cushion 71. The sonic vibrator assembly 76 includes, among others, the following components: two electrodes, a piezoceramic disc, and wire leads.

Figure 9A:
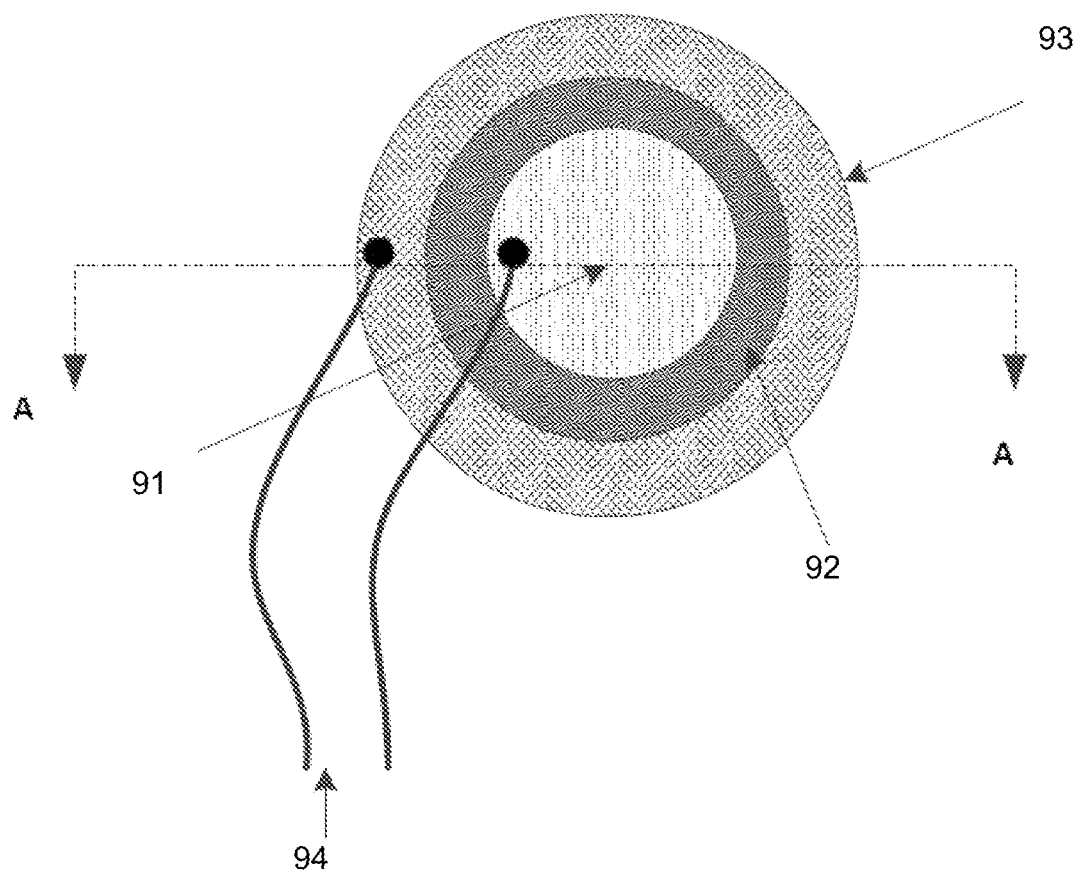
FIG. 9A shows a radial view of an example Sonic Vibrator Assembly.
Figure 9B:
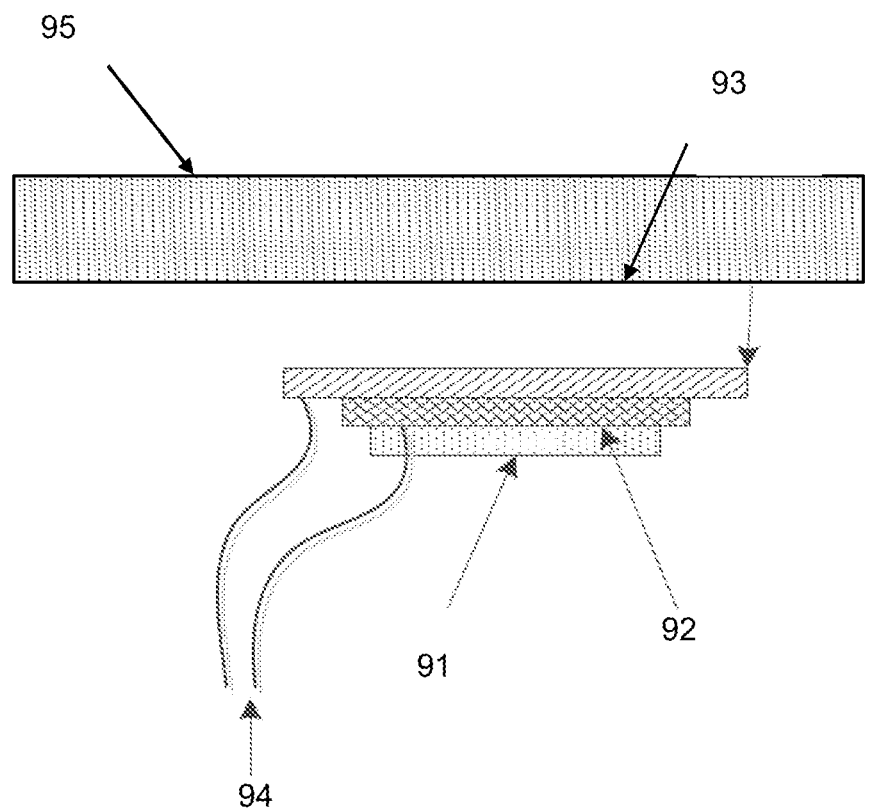
FIG. 9B shows a cross-sectional view of an example Sonic Vibrator Assembly.

Piezoelectric materials, such as, for example, the piezoceramic disc, have the ability to generate a voltage in response to an applied mechanical stress or conversely change shape in response to an applied voltage. In some implementations, the piezoceramic disc may be composed of high power "hard" materials, high sensitivity "soft" materials, or high performance piezoelectric crystals. In some implementations, an example of which is shown in FIGS. 9A and 9B, the piezoceramic disc 92 is sandwiched between two electrodes (91 and 93), and lead wires 94 are attached to each electrode (91 and 93). In some implementations, the electrodes 91 and 93 are composed of metal. In a further implementation, the electrodes 91 and 93 of the sonic vibration assembly 76 comprise a silver electrode and a brass plate. FIGS. 9A and 9B show an implementation where one side of the piezoceramic disc 92 is adhered to a brass plate electrode 93, while the opposite side of the piezoceramic disc 92 is adhered to a silver electrode 91. As shown in FIG. 9B, the brass plate electrode 93 is affixed to the flexible non-heat conducting layer, i.e. the cushion 95. In some implementations, as shown in FIG. 9A, the radius of the brass plate electrode 93 is larger than that of the piezoceramic disc 92 and the silver electrode 91.

When an alternating voltage signal with a certain frequency is applied to the leads 94, the alternating potential difference between the two electrodes, namely the silver electrode 91 and the brass plate electrode 93, causes the piezoceramic disc 92 to mechanically expand or contract in the radial direction at substantially the same frequency as that of the applied alternating voltage signal. This resulting radial expansion and contraction of the piezoceramic disc 92 causes the brass plate electrode 93 to vibrate with the piezoceramic disc 92. These vibrations in the brass plate electrode 93 can, in turn, be transferred to the cushion to which the brass plate electrode 93 is adhered. Thus, application of a low frequency alternating signal (e.g., 10 Hz) to the piezoceramic disk 92 can, in effect, cause the brass plate electrode 93 to vibrate at substantially the same low frequency, thereby permitting a low frequency vibrations to propagate through the cushion 95 and create an agitation effect. In some implementations, the thickness of the electrode that makes contact with the cushion 95 (e.g., the brass plate electrode 93 in FIG. 9B) can, in part, affect the amplitude of the vibrations transferred to the cushion. In some implementations, the thickness of the brass plate electrode 93 in FIG. 9B ranges from about 0.5 mm to about 1 mm. In some implementations, the brass plate electrode 93 in FIG. 9B is 0.5 mm thick. In some implementations, the brass plate electrode 93 in FIG. 9B is 1 mm thick.

Figure 8:
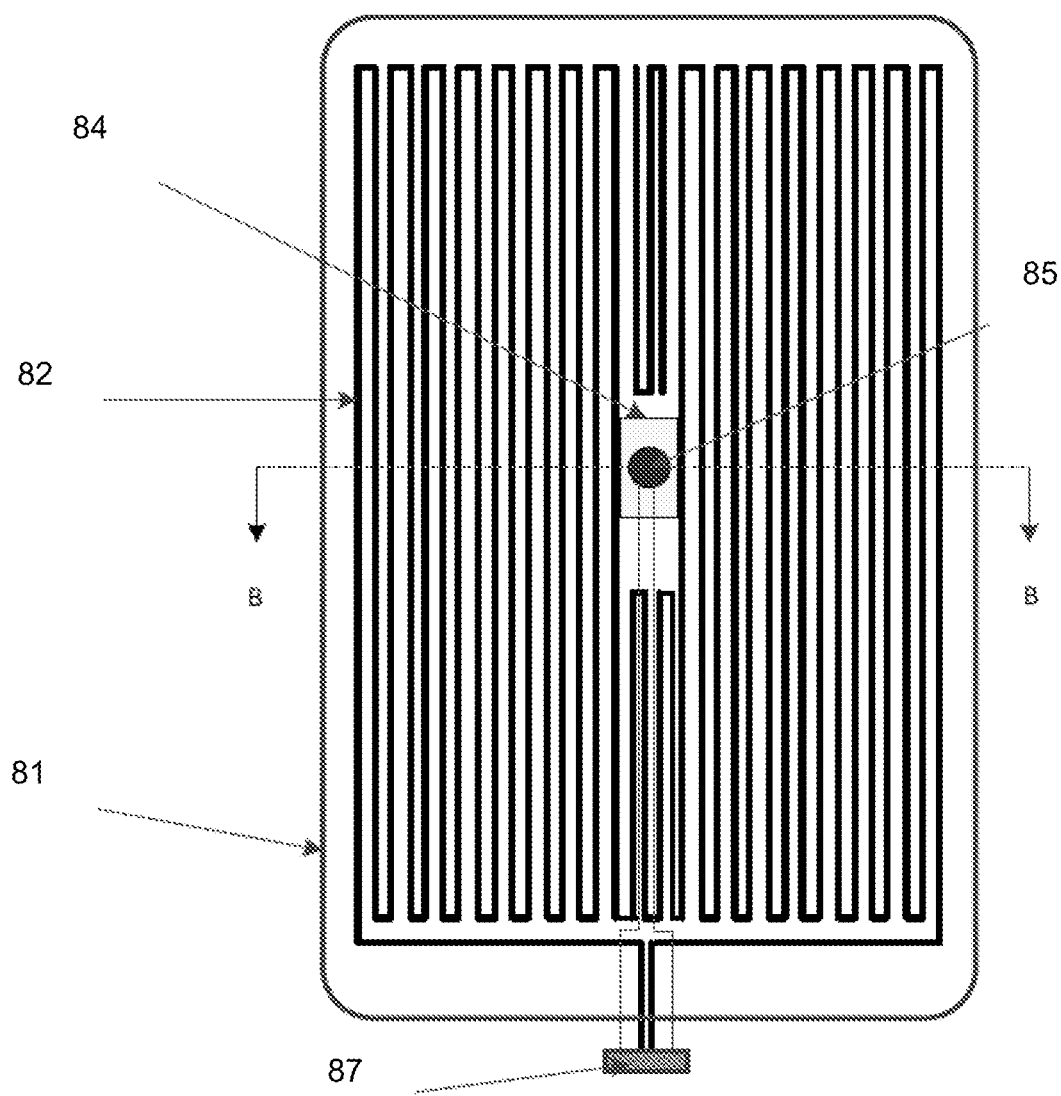
FIG. 8 shows another view of an example cushion device 80.

The electrical power requirements of the heating element and the temperature sensor(s) can be supplied via an electronic connector. For example, FIG. 8 shows another view of an example cushion device 80. The cushion device 80 includes a cushion 81, a high density heating element 82, a temperature sensor 85 disposed between a heat insulation barrier 84. Wires from the high density heating element 82 and the temperature sensor 95 affixed into an electronic connector 87 that is configured to connect to a power source (not shown) and a controller (not shown).

Dry Thawing Using the Cushion Device

Figure 11:
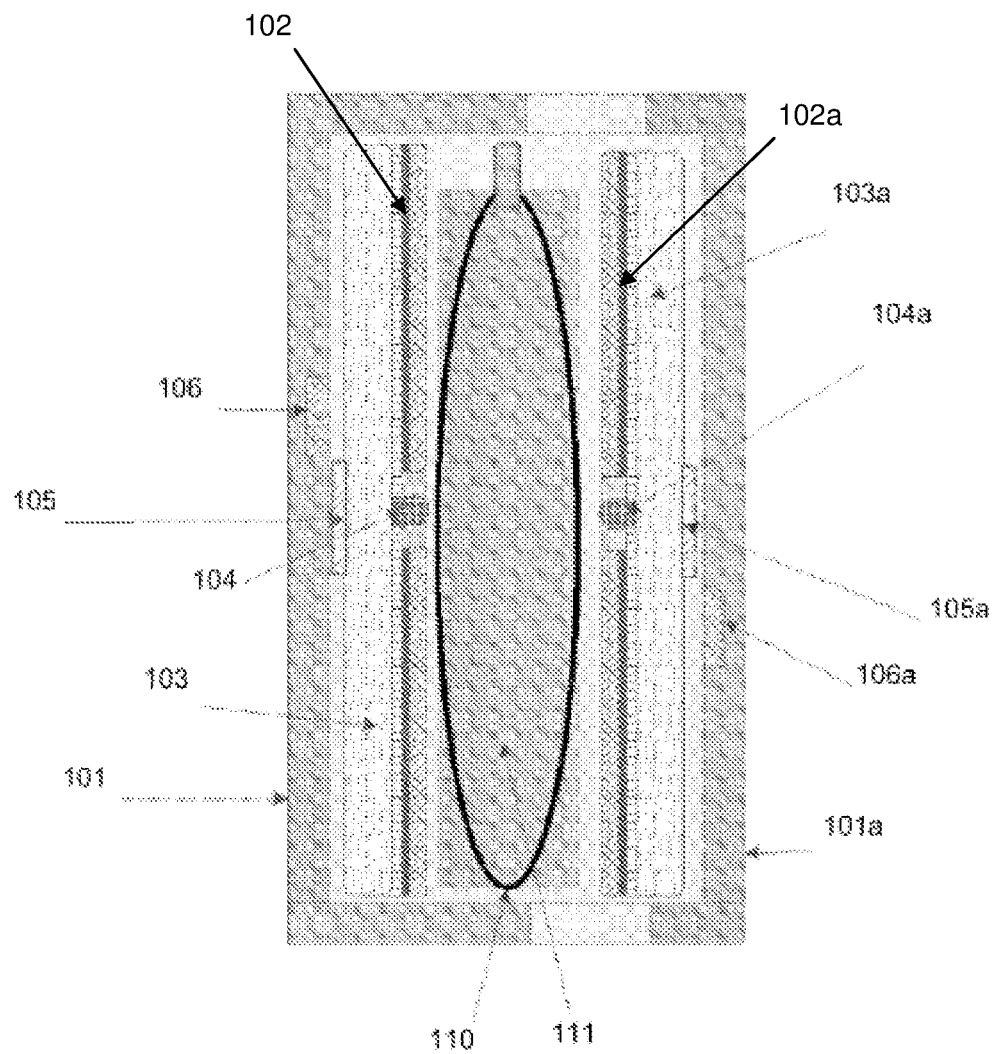
FIG. 11 illustrates the side view of the dry heat thawing chamber.

FIGS. 10 and 11 show a top view and a side view, respectively, of a dry heat thawing chamber 100. The dry heat thawing chamber 100 includes a first side chamber 101 and an adjustable second side chamber 101a. The first side chamber 101 includes a first cushion device 103, a first heating element 102, a first temperature sensor 104, a first sonic vibrator assembly 105, a first heat insulation barrier 107, a first heat conducting sheet 108, and a first radio-frequency (RF) reader 106. The adjustable second side chamber 101a includes a second cushion device 103a, a second heating element 102a, a second temperature sensor 104a, a second sonic vibrator assembly 105a, a second heat insulation barrier 107a, a second heat conducting sheet 108a, and a second RF reader 106a. The thawing chamber 100 also includes a front end control (FEC) board 109. FIGS. 10 and 11 also show an overlap bag 110 containing an enclosed bag 111.

As shown in FIGS. 10 and 11, the bag 111 containing medication, plasma, whole blood, glycerolized blood, RBCs or any other biological substance is placed in the space between the two flexible heat conducting sheets 108 and 108a of the first and second cushion devices 103 and 103a. When powered with electrical current, the high-density heating elements 102 and 102a produce thermal energy which diffuses into the flexible heat conducting sheets 108 and 108a. At the onset of the thawing process, heat is transferred from the flexible heat conducting sheets 108 and 108a to the bag 111 in need of thawing by conduction. Thermal convective flow may take prominence as the biological substance near the heated walls of the bag 111 becomes liquefied. The low frequency vibrations produced by the sonic vibrator assemblies 105 and 105a prevent concentration gradients from being formed during the thawing process and helps achieve an almost homogenous temperature profile within the bag. Additionally, temperature sensors 104 and 104a measure the temperature of the bag 111 and communicate the measurements to a controller via the electronic connector during the thawing process. The dry thawing process can be terminated as soon as the bag 111 containing the biological substance reaches a desired temperature, thereby reducing the risk of overheating, under-thawing, and denaturation, and increasing the efficiency of the thawing process. In some embodiments, a standard 250 ml-500 ml bag containing plasma, whole blood, glycerolized blood bag, and/or other biological substances with a starting temperature of −40° C. can be thawed to 36.6° C. within 10 minutes when the cushion device is powered with electrical current. In some embodiments, a standard 250 ml-500 ml bag containing plasma, whole blood, glycerolized blood bag, and/or other biological substances with a starting temperature of −40° C. can be thawed to 36.6° C. within 5 minutes when the cushion device is powered with electrical current.

The disclosed dry thawing device confers several advantages: (1) reduced risk of microbial contamination compared to thawing methods involving water-baths, (2) uniform thawing of the biological substance resulting in reduced risk of overheating, underthawing or denaturation, (3) low maintenance compared to conventional water baths and water bladders.

As shown in FIGS. 10 and 11, the perimeter of the flexible heat conducting sheets 108 and 108a is larger than the perimeter of the bag 111 containing the biological substance. In other embodiments, the perimeter of the flexible heat conducting sheets 108 and 108a is the same as the perimeter of the bag 111 containing biological substances.

Dry Heat Thawing Chamber

Figure 13:
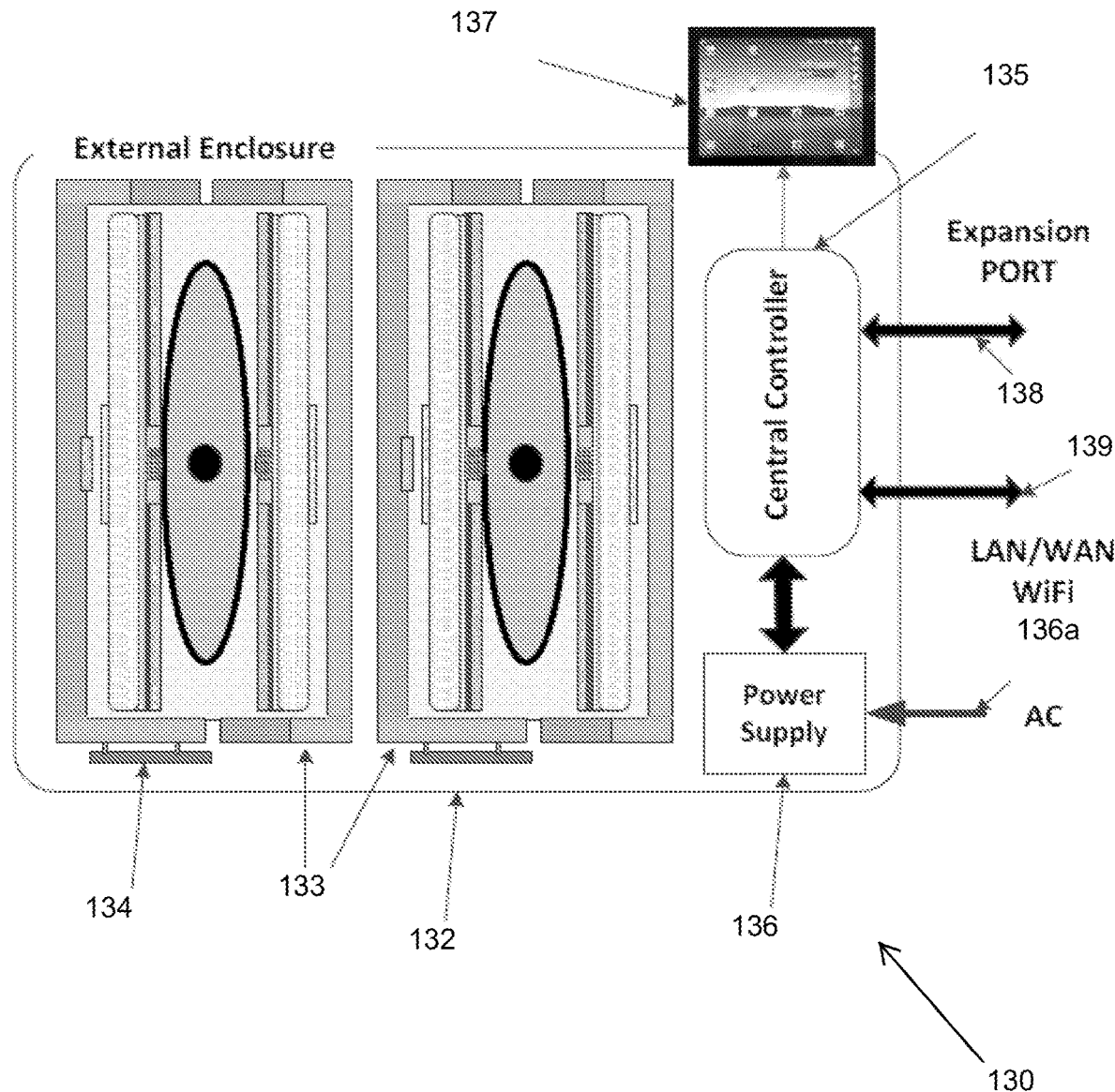
FIG. 13 is a block diagram of a device comprising two typical dry heat thawing chambers (top view).

The present technology discloses an apparatus that implements a modular, computerized, closed-loop dry thawing process and is configured to have at least two separate thawing chambers. Each thawing chamber is a self-contained unit that can be altered or replaced without affecting the remainder of the system. FIG. 13 shows a schematic of an example modular dry thawing apparatus 130. In particular, FIG. 13 shows a main module 132 including two separate thawing chambers 133. Each thawing chamber 133 can be implemented using the dry heat thawing chamber 100 discussed above in relation to FIGS. 10 and 11. The main module 132 also includes a central controller 135, a universal power supply 136, and a graphical user interface or display 137. The central controller 135 can include a control program for controlling the thawing chambers 133. The central controller can receive data received from the RF readers and provide control signals to the thawing chambers 133. The central controller 135 can also include expansion ports 138 for connecting auxiliary modules, and include communication ports 139 for providing communication to external devices. The power supply 136 can receive AC power 136 and provide one or more AC or DC voltages and currents to the various components of the main module 132 (and any auxiliary modules).

FIG. 14 shows a schematic of another modular dry thawing apparatus 140 including at least two modules: a main module 132 and an auxiliary module 132a. The auxiliary module 132a can be used as an expansion module and connect into and controlled by the main module 132. The auxiliary module 132a can allow adding capacity to the modular dry thawing apparatus 140.

As shown in FIGS. 13 and 14, individual thawing chambers 133 of the main module 132 or auxiliary module 132a may be encompassed within their respective external enclosures. In some embodiments, the main module 132 of the computerized closed-loop dry thawing system 130 has a two chamber configuration. In other embodiments, the main module 132 of the computerized closed-loop dry thawing system has a four chamber configuration. In another embodiment, the main module 132 of the computerized closed-loop dry thawing system has an eight chamber configuration. Generally, the main module 132 can include any number of dry heat thawing chambers 133.

As seen in FIG. 14, a thawing chamber 133 is a three-dimensional rectangular compartment that encloses two dry thawing cushion devices. In some embodiments, the exterior of the thawing chamber is composed of plastic, metal, or a metal alloy (e.g., stainless steel). In other embodiments, the thawing chamber has a bacteria-resistant powder coated exterior. As discussed above, in relation to FIGS. 10 and 11, the dry thawing device comprises two cushion devices wherein the heat conducting portion of the first cushion device faces the heat conducting portion of the second cushion device. FIG. 14 shows an implementation where one of the elongated side walls of the thawing chamber 133 is adjustable. In such an implementation, the components of the cushion device (i.e., the flexible non-heat conducting layer, flexible heat conducting sheet, heating element, temperature sensor, sonic vibrator assembly, and heat insulation barrier) that are contiguous to the adjustable side wall are also adjustable. This feature permits the flexible heat conducting sheets of the thawing device to properly contact the walls of a bag containing biological substances, regardless of the volume of the bag. A detailed description regarding the structural components of the cushion device and its operation is discussed above.

In some embodiments, RF readers are embedded in the interior walls of the thawing chamber 133. Fixed RF readers are set up to create a specific interrogation zone which can be tightly controlled. Here, the interrogation zone would be the space between the two flexible heat conducting sheets of the first and second cushion devices. This designated space acts as a repository for bags that incorporate RFID tags and are used for storing biological substances. This allows a highly defined reading area for when RFID tags go in and out of the interrogation zone. The RF readers embedded in the interior walls of each thawing chamber serve to (a) power the on-board RFID tags of (i) overwrap bags and (ii) bags containing biological substances with Smart Labels affixed to their outer wall, through electromagnetic induction from the RF reader antenna and (b) wirelessly detect the electromagnetic radiation emitted by these RFID tags and interpret these signals as meaningful data. In some embodiments, the thawing chamber 133 can be used for thawing bags such as the smart bag 10 shown in FIG. 1, the overwrap bag 50 shown in FIG. 5, and bags having a Smart label discussed above in relation to FIG. 6.

Figure 12:
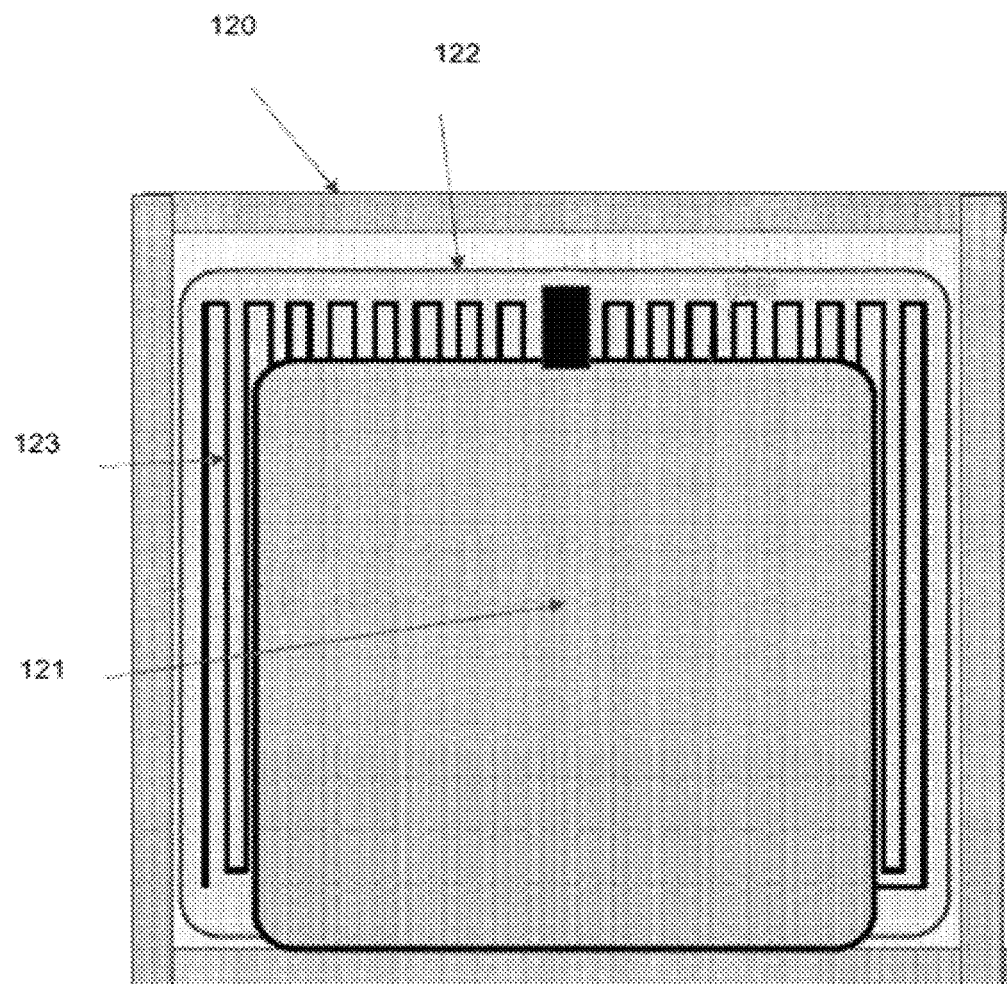
FIG. 12 shows an implementation where a thawing chamber is used to thaw a bag without an integrated sensor or RF device.

In some embodiments, the thawing chamber 133 also can be used for thawing bags that lack integrated sensors and/or RF devices. For example, FIG. 12 shows an implementation where a thawing chamber 120 is used to thaw a bag 121 without an integrated sensor or RF device. The bag 120 is placed on a cushion 122 including a high density heating element 123. The cushion 122 can be similar to the cushion device 80 discussed above in relation to FIG. 8. That is, the cushion 122 can include a temperature sensor for sensing the temperature of the bag 120, and an RFID for transmitting the sensed temperature to a RF reader. In some embodiments, the bag 120 may also be enclosed in an overlap bag, such as the one discussed above in relation to FIG. 5.

In other implementations, the chamber 133 can be used for thawing bags that incorporate a sensor configured to measure temperature of the bag and a radio-frequency (RF) device communicably coupled to the sensor and configured to: (a) acquire from the sensor data associated with the measured temperatures, (b) store the acquired sensor data in nonvolatile memory, and (c) communicate the stored temperature data wirelessly to a RF reader (i.e., a Smart Label). One example of such a bag is discussed above in relation to FIG. 1. In some embodiments, the sensor and the RF device are affixed to the outer wall of the bag. In some embodiments, the sensor and the RF device are affixed to the inner wall of the bag. In some embodiments, the sensors and RF devices affixed to the inner wall of the bag sense and store additional physical and physiological parameters including source history, identification, demographics, time stamping, temperature, pH, conductivity, glucose, $O_2$, $CO_2$ levels, which can subsequently be communicated wirelessly to a RF reader.

In some embodiments, the thawing chamber 133 may be used to thaw bags containing biological substances that are enclosed and protected by overwrap bags, one example of which is discussed above in relation to FIG. 5. These overwrap bags incorporate a sensor configured to measure temperature of the enclosed bags containing biological substances and a radio-frequency device communicably coupled to the sensor and configured to: (a) acquire from the sensor data associated with the measured temperatures, (b) store the acquired sensor data in nonvolatile memory, and (c) communicate the stored temperature data wirelessly to a RF reader.

In some embodiments, each thawing chamber 133 can include a front end control board 134 that permits direct user-interaction with the thawing chamber 133. In some embodiments, the front end control board 134 comprises a chamber temperature display, bag temperature display, one or more timer displays, controls for setting or adjusting chamber temperature, a heating status visual indicator, controls for setting or adjusting sonic vibration parameters, and a power switch. In some implementations, the sonic vibration controls permit users to manually input the desired frequency (Hz) and timing of the sonic vibrator assembly. In some implementations, the front end control board 134 contains controls permitting the user to set a program sequence for sonic vibration and/or temperature modulation. In some implementations, the front end control board 134 contains controls that permit users to manually start or stop sonic vibration and/or heating at any point during the thawing process. In some implementations, the front end control board 134 contains an audiovisual alarm that indicates when the bag temperature reaches the desired temperature (e.g., 36.6° C.).

Figure 18:
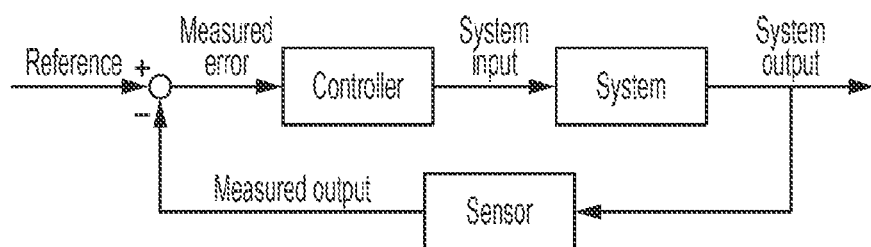
FIG. 18 shows a block diagram of an example closed-loop system.

FIG. 18 shows a block diagram of an example closed-loop system. A closed-loop system refers to a system which compares an output variable of a system to a certain reference value and manipulates the inputs of a system to obtain the desired effect on the output of the system.

The modular dry thawing apparatus 130, and in particular the central controller 135, shown in FIG. 13 can utilize a closed-loop dry thawing method. For example, the closed-loop dry thawing method can utilize the example closed loop system shown in FIG. 18. First, temperature sensors monitor the system output (temperature) of a bag containing biological substances in each thawing chamber 133 and transmit the data to the central controller 135. The central controller 135 then transforms the data and compares it to a preset value, e.g., the desired temperature, and subsequently adjusts the system input (electrical current) as necessary to thaw the bag and achieve the desired temperature. The central controller affects the temperature of the bag, which in turn is measured and looped back to alter the control.

As shown in FIGS. 13 and 14, the universal power supply 136 drives electrical current to all electrical components of the dry thawing apparatus including the sonic vibrator assembly, the high density heating filament, and the built-in temperature sensors of the cushion device, the RF readers of the thawing chambers 133, the central controller, and the graduated AC/DC power supply. In some implementations, the universal power supply 136 drives electrical current to the graphic user interface 137.

As shown in FIGS. 13 and 14, the central controller 135 controls all functional aspects of the disclosed dry thawing apparatus 130 and 140. The central controller 135 acquires from the temperature sensors of the cushion devices data associated with recurring measured temperatures, transforms and compares the acquired data to the preset temperature value, and generates an error signal by subtracting the sensed value from the preset temperature value. The central controller 135 then responds to the generated error signal by regulating the electrical current supplied to the high density heating elements in a particular thawing chamber 133 until the bag achieves the preset temperature value. The central controller 135 can also adjust the electrical current supplied to the high density heating elements in a given thawing chamber 133 based on input that is manually entered by the user. In some implementations, user input can be directly entered into the central controller 135. In other implementations, user input can be entered through a remote device that is linked to the central controller 135 via a LAN/WAN Wifi network 136*a*. In some implementations, the central controller 135 communicates with the graduated AC/DC power supply 136 to regulate the electrical current supplied to a thawing chamber 133. In some implementations, the central controller 135 will automatically shut off electrical power to flexible heat conducting sheets within a particular thawing chamber 133 once the bag containing biological substances reaches the desired temperature. In some implementations, the central controller 135 will trigger an audio and/or visual alarm chamber once the bag containing biological substances reaches the desired temperature.

The central controller 135 is also communicably coupled to RF readers that are embedded in the interior walls of the thawing chamber 133. This feature permits the central controller 135 to read and interpret any data acquired from RFID tags that are affixed to overwrap bags or bags containing biological substances (i.e., bags including Smart Labels) in the thawing chamber 133. The central controller acquires from the RF readers data associated with recurring measured temperatures, transforms and compares the acquired data to the preset temperature value, and generates an error signal by subtracting the sensed value from the preset temperature. The central controller then responds to the generated error signal by regulating the electrical current supplied to the high density heating elements in a particular thawing chamber 133 until the bag achieves the preset temperature value. The central controller 135 can also adjust the electrical current supplied to the high density heating elements in a given thawing chamber 133 based on input that is manually entered by the user. In some implementations, user input can be directly entered into the central controller 135. In other implementations, user input can be entered through a remote device that is linked to the central controller via a LAN/WAN Wifi network. In some implementations, the central controller 135 communicates with the graduated AC/DC power supply 136 to regulate the electrical current supplied to a thawing chamber. In some implementations, the central controller 135 will automatically shut off electrical power to flexible heat conducting sheets within a particular thawing chamber once the bag containing biological substances reaches the desired temperature.

The central controller 135 also displays sensor output on a graphic user interface (GUI) 137. In some embodiments, the GUI 137 is a smart phone, personal digital assistant, a laptop LCD monitor, or a desktop LCD monitor. Alternatively, the central controller 135 can communicate sensor output wirelessly to a remote device using a LAN/WAN WiFi network.

Expansion ports 138 add functionality to a computer system via a collection of wires and protocols. As shown in FIG. 14, the computerized closed-loop system utilizes an expansion port 138, which facilitates movement of information between the central controller 135 and auxiliary thawing chambers 133 in the auxiliary module 132*a* that are separate and distinct from the main module 132 of the dry thawing apparatus 140. As a result, the central controller 135 can monitor and regulate the auxiliary thawing chambers 133 in a manner identical to that of the thawing chambers 133 within the main module 132 of the dry thawing apparatus. In some embodiments, the expansion port 138 is a serial port. In some embodiments, the expansion port 138 is selected from the group consisting of: serial port, parallel port, USB port and multi-I.O cards. In some embodiments, the auxiliary module 132*a* of the computerized closed-loop dry thawing system 140 has a two chamber configuration. In some embodiments, the auxiliary module 132*a* of the computerized closed-loop dry thawing system has a four chamber configuration. In some embodiments, the auxiliary module 132*a* of the computerized closed-loop dry thawing system has a six chamber configuration. In some embodiments, the auxiliary module 132*a* of the computerized closed-loop dry thawing system has an eight chamber configuration. In some embodiments, the auxiliary module 132*a* of the computerized closed-loop dry thawing system has a ten chamber configuration. In some embodiments, the auxiliary module 132*a* of the computerized closed-loop dry thawing system has a twelve chamber configuration. Generally, the auxiliary module 132*a* can include any number of dry heat thawing chambers 133*a*.

In some implementations, the RFID tag may be implemented on a system-on-chip (SOC). In some other implementations, the RFID tag may be implemented using discrete components.

As used herein, the term "about" in reference to a number is generally taken to include numbers that fall within a range of 5%, 10%, 15%, or 20% in either direction (greater than or less than) of the number unless otherwise stated or otherwise evident from the context.

As used herein, the terms "cushion" and "flexible non-heat conducting layer" are used interchangeably throughout the specification.

The term "temperature sensing module" refers to an electronic device configured to come into contact with a bag containing biological substances, including a sensor configured to measure temperature of the bag containing biological substances, and a radio-frequency (RF) device communicably coupled to the temperature sensor and configured to: (a) acquire from the sensor data associated with the measured temperatures, (b) store the acquired sensor data in nonvolatile memory, and (c) communicate the stored data wirelessly to a RF reader.

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

What is claimed is:

1. A device for thawing a biological substance, comprising: a reversibly sealable housing defining a chamber, wherein the housing comprises a plurality of cushion devices and each of the plurality of cushion devices comprises: a heating element configured to generate thermal energy, a flexible first layer in direct contact with the heating element; and a temperature sensor.

2. The device of claim 1, wherein each of the plurality of cushion devices further comprises: a sonic vibrator assembly configured to mechanically agitate a biological substance contained within an enclosure that is received within the chamber; and a flexible second layer interposed between the sonic vibrator assembly and the heating element, wherein the second layer is configured to inhibit thermal communication between the sonic vibrator assembly and the heating element.

3. The device of claim 2, wherein the sonic vibrator assembly and the heating element are configured to simultaneously heat and mechanically agitate a biological substance contained within an enclosure that is received within the chamber.

4. The device of claim 1 further comprising a radio frequency (RF) reader configured to interrogate a radio frequency ID tag (RFID) positioned within the chamber.

5. The device of claim 1, wherein each temperature sensor comprises a cushion temperature sensor that is thermally insulated from thermal energy generated by the respective heating element in each of the plurality of cushion devices.

6. The device of claim 5, wherein each cushion temperature sensor is positioned to be adjacent to an exterior surface of an enclosure containing a biological substance that is received within the chamber.

7. The device of claim 1 further comprising an enclosure containing a biological substance positioned within the chamber, wherein the enclosure comprises an enclosure temperature sensor.

8. The device of claim 7, wherein the enclosure further comprises an RFID tag.

9. The device of claim 7, wherein the enclosure temperature sensor is in direct contact with the biological substance contained within the enclosure.

10. The device of claim 7, wherein the enclosure is a reversibly sealable overwrap bag enclosing a bag containing a biological substance, wherein the enclosure temperature sensor is configured to measure a temperature of the bag containing the biological substance.

11. The device of claim 1, wherein a first cushion device of the plurality of cushion devices and a second cushion device of the plurality of cushion devices are positioned opposite one another such that the first layer of the first cushion device faces the first layer of the second cushion device.

12. The device of claim 1, wherein the chamber further comprises a first side chamber dimensioned to receive a first cushion device of the plurality of cushion devices and a second side chamber configured to receive a second cushion device of the plurality of cushion devices, wherein a position of the second side chamber is adjustable with respect to the first side chamber.

13. The device of claim 1 further comprising a controller in communication with each heating element, wherein the controller comprises instructions to regulate thermal energy generated by each heating element based upon a measured temperature.

14. A device for thawing a biological substance, comprising; a reversibly sealable housing defining a chamber configured to receive an enclosure containing a biological substance to be thawed, wherein the housing comprises a plurality of cushion devices and each of the plurality of cushion devices comprises: a cushion; a heating element coupled to the cushion and configured to generate thermal energy; and a temperature sensor positioned to be adjacent to the enclosure containing the biological substance to be thawed when the enclosure is received within the chamber.

15. The device of claim 14 further comprising a radio frequency (RF) reader configured to interrogate a radio frequency ID tag (RFID) positioned within the chamber.

16. The device of claim 14, wherein each temperature sensor is thermally insulated from thermal energy generated by the respective heating element in each of the plurality of cushion devices.

17. The device of claim 14 further comprising the enclosure containing the biological substance to be thawed positioned within the chamber, wherein the enclosure comprises an enclosure temperature sensor.

18. The device of claim 17, wherein the enclosure further comprises an RFID tag.

19. The device of claim 17, wherein the enclosure temperature sensor is in direct contact with the biological substance contained within the enclosure.

20. The device of claim 17, wherein the enclosure is a reversibly sealable overwrap bag enclosing a bag containing the biological substance, wherein the enclosure temperature sensor configured to measure a temperature of the bag containing the biological substance.

21. The device of claim 14, wherein a first cushion device of the plurality of cushion devices and a second cushion device of the plurality of cushion devices are positioned opposite one another such that a first layer of the first cushion device faces a first layer of the second cushion device.

22. The device of claim 14, wherein the chamber further comprises a first side chamber dimensioned to receive the first cushion device and a second side chamber configured to receive the second cushion device, wherein a position of the second side chamber is adjustable with respect to the first side chamber.

23. The device of claim 14 further comprising a controller in communication with each heating element, wherein the controller comprises instructions to regulate thermal energy generated by each heating element based upon a measured temperature.

* * * * *